United States Patent
Dinville et al.

(10) Patent No.: US 10,195,046 B2
(45) Date of Patent: *Feb. 5, 2019

(54) INSTRUMENTS AND METHODS FOR REMOVING FIXATION DEVICES FROM INTERVERTEBRAL IMPLANTS

(71) Applicant: LDR Medical, Rosières près Troyes (FR)

(72) Inventors: Hervé Dinville, St. Parres aux Tertres (FR); Samuel LeQuette, Toulouse (FR); Emmanuel Bougère, Troyes (FR)

(73) Assignee: LDR Medical, Rosieres pres Troyes (FR)

( * ) Notice: Subject to any disclaimer, the term of this patent is extended or adjusted under 35 U.S.C. 154(b) by 275 days.

This patent is subject to a terminal disclaimer.

(21) Appl. No.: 14/931,007

(22) Filed: Nov. 3, 2015

(65) Prior Publication Data

US 2016/0051380 A1    Feb. 25, 2016

Related U.S. Application Data

(63) Continuation of application No. 13/158,761, filed on Jun. 13, 2011, now Pat. No. 9,173,745, which is a
(Continued)

(51) Int. Cl.
*A61F 2/44*    (2006.01)
*A61F 2/46*    (2006.01)
(Continued)

(52) U.S. Cl.
CPC ........ *A61F 2/4455* (2013.01); *A61B 17/7074* (2013.01); *A61B 17/7076* (2013.01);
(Continued)

(58) Field of Classification Search
CPC .......... A61F 2/44; A61F 2/442; A61F 2/4455; A61F 2/46; A61F 2/4603; A61F 2/4611;
(Continued)

(56) References Cited

U.S. PATENT DOCUMENTS

| | | |
|---|---|---|
| 344,683 A | 6/1886 | Sherer |
| 1,025,596 A | 5/1912 | Strawser |

(Continued)

FOREIGN PATENT DOCUMENTS

| | | |
|---|---|---|
| AU | 2009357504 A1 | 7/2016 |
| AU | 2016203916 A1 | 7/2016 |

(Continued)

OTHER PUBLICATIONS

"U.S. Appl. No. 10/276,712, Advisory Action dated Feb. 8, 2006", 3 pgs.
(Continued)

*Primary Examiner* — Larry E Waggle, Jr.
(74) *Attorney, Agent, or Firm* — Schwegman, Lundberg & Woessner, P.A.

(57) ABSTRACT

Anchor removal instruments and methods for using the instruments are provided. In some embodiments, an intervertebral implant anchor extractor tool comprises a support, a support retainer configured to hold the support fixed with respect to the implant, an extractor having an anchor retainer, and an extractor guide. An embodiment of a method of using this implant anchor extractor tool comprises the steps of obtaining access to an anchor, grasping the anchor, and applying a withdrawal force on the anchor while applying a countervailing force against the implant or a vertebral structure.

16 Claims, 12 Drawing Sheets

Related U.S. Application Data continuation-in-part of application No. PCT/IB2009/008048, filed on Dec. 31, 2009.

(51) Int. Cl.
  *A61B 17/84* (2006.01)
  *A61B 17/70* (2006.01)
  *A61F 2/30* (2006.01)

(52) U.S. Cl.
  CPC ............ *A61B 17/84* (2013.01); *A61B 17/846* (2013.01); *A61F 2/44* (2013.01); *A61F 2/442* (2013.01); *A61F 2/447* (2013.01); *A61F 2/4425* (2013.01); *A61F 2/46* (2013.01); *A61F 2/4603* (2013.01); *A61F 2/4611* (2013.01); *A61F 2/4637* (2013.01); *A61F 2002/30401* (2013.01); *A61F 2002/30403* (2013.01); *A61F 2002/30428* (2013.01); *A61F 2002/30472* (2013.01); *A61F 2002/30576* (2013.01); *A61F 2002/30578* (2013.01); *A61F 2002/30579* (2013.01); *A61F 2002/30604* (2013.01); *A61F 2002/30782* (2013.01); *A61F 2002/30785* (2013.01); *A61F 2002/30787* (2013.01); *A61F 2002/30879* (2013.01); *A61F 2002/30889* (2013.01); *A61F 2002/4475* (2013.01); *A61F 2002/4615* (2013.01); *A61F 2002/4619* (2013.01); *A61F 2002/4623* (2013.01); *A61F 2002/4629* (2013.01); *A61F 2002/4641* (2013.01); *A61F 2220/0008* (2013.01); *A61F 2220/0016* (2013.01); *A61F 2220/0025* (2013.01); *A61F 2220/0041* (2013.01)

(58) Field of Classification Search
  CPC ...... A61F 2002/4615; A61F 2002/4619; A61F 2002/4623; A61F 2/4637; A61F 2002/4641; A61F 2220/0008; A61F 2220/0016
  See application file for complete search history.

(56) References Cited

U.S. PATENT DOCUMENTS

| | | |
|---|---|---|
| 1,121,484 A | 12/1914 | Crites |
| 3,374,786 A | 3/1968 | Callender, Jr. |
| 3,791,380 A | 2/1974 | Dawidowski |
| 3,875,595 A | 4/1975 | Froning |
| 3,892,232 A | 7/1975 | Neufeld |
| 3,948,262 A | 4/1976 | Zaffaroni |
| 4,009,712 A | 3/1977 | Burstein et al. |
| 4,135,506 A | 1/1979 | Ulrich |
| 4,175,555 A | 11/1979 | Herbert |
| 4,237,875 A | 12/1980 | Termanini |
| 4,349,921 A | 9/1982 | Kuntz |
| 4,379,451 A | 4/1983 | Getscher |
| 4,409,974 A | 10/1983 | Freedland et al. |
| 4,432,358 A | 2/1984 | Fixel |
| 4,488,543 A | 12/1984 | Tornier |
| 4,494,535 A | 1/1985 | Haig |
| 4,507,115 A | 3/1985 | Kambara et al. |
| 4,519,100 A | 5/1985 | Wills et al. |
| 4,561,432 A | 12/1985 | Mazor |
| 4,599,086 A | 7/1986 | Doty |
| 4,612,920 A | 9/1986 | Lower |
| 4,621,629 A | 11/1986 | Koeneman |
| 4,632,101 A | 12/1986 | Freedland |
| 4,653,489 A | 3/1987 | Tronzo |
| 4,657,001 A | 4/1987 | Fixel |
| 4,714,469 A | 12/1987 | Kenna |
| 4,721,103 A | 1/1988 | Freedland |
| 4,759,352 A | 7/1988 | Lozier |
| 4,787,378 A | 11/1988 | Sodhi |
| 4,790,303 A | 12/1988 | Steffee |
| 4,791,918 A | 12/1988 | Von Hasselbach |
| 4,834,757 A | 5/1989 | Brantigan |
| 4,863,476 A | 9/1989 | Shepperd |
| 4,892,545 A | 1/1990 | Day et al. |
| 4,898,156 A | 2/1990 | Gatturna et al. |
| 4,904,261 A | 2/1990 | Dove et al. |
| 4,946,468 A | 8/1990 | Li |
| 4,964,403 A | 10/1990 | Karas et al. |
| 4,968,315 A | 11/1990 | Gatturna |
| 4,969,887 A | 11/1990 | Sodhi |
| 4,973,332 A | 11/1990 | Kummer |
| 4,973,333 A | 11/1990 | Treharne |
| 4,997,432 A | 3/1991 | Keller |
| 5,002,550 A | 3/1991 | Li |
| 5,007,910 A | 4/1991 | Anapliotis et al. |
| 5,032,125 A | 7/1991 | Durham et al. |
| 5,041,114 A | 8/1991 | Chapman et al. |
| 5,041,116 A | 8/1991 | Wilson |
| 5,046,513 A | 9/1991 | Gatturna et al. |
| 5,057,103 A | 10/1991 | Davis |
| 5,062,851 A | 11/1991 | Branemark |
| 5,087,266 A | 2/1992 | Connell et al. |
| 5,098,433 A | 3/1992 | Freedland |
| 5,116,336 A | 5/1992 | Frigg |
| 5,129,901 A | 7/1992 | Decoste |
| 5,176,681 A | 1/1993 | Lawes et al. |
| 5,192,303 A | 3/1993 | Gatturna et al. |
| 5,192,327 A | 3/1993 | Brantigan |
| 5,197,986 A | 3/1993 | Mikhail |
| 5,207,679 A | 5/1993 | Li |
| 5,217,486 A | 6/1993 | Rice et al. |
| 5,242,448 A | 9/1993 | Pettine et al. |
| 5,246,458 A | 9/1993 | Graham |
| 5,300,074 A | 4/1994 | Frigg |
| 5,306,307 A | 4/1994 | Senter et al. |
| 5,306,309 A | 4/1994 | Wagner et al. |
| 5,314,477 A | 5/1994 | Marnay |
| 5,324,292 A | 6/1994 | Meyers |
| 5,326,205 A | 7/1994 | Anspach, Jr. et al. |
| 5,342,394 A | 8/1994 | Matsuno et al. |
| 5,356,410 A | 10/1994 | Pennig |
| 5,356,413 A | 10/1994 | Martins et al. |
| 5,358,526 A | 10/1994 | Tornier |
| 5,372,599 A | 12/1994 | Martins |
| 5,397,364 A | 3/1995 | Kozak et al. |
| 5,401,269 A | 3/1995 | Buttner-janz et al. |
| 5,417,692 A | 5/1995 | Goble et al. |
| 5,417,712 A | 5/1995 | Whittaker et al. |
| 5,425,772 A | 6/1995 | Brantigan |
| 5,429,641 A | 7/1995 | Gotfried |
| 5,437,674 A | 8/1995 | Worcel |
| 5,443,514 A | 8/1995 | Steffee |
| 5,456,721 A | 10/1995 | Legrand |
| 5,458,601 A | 10/1995 | Young, Jr. et al. |
| 5,458,638 A | 10/1995 | Kuslich et al. |
| 5,472,452 A | 12/1995 | Trott |
| 5,478,342 A | 12/1995 | Kohrs |
| 5,489,210 A | 2/1996 | Hanosh |
| 5,501,695 A | 3/1996 | Anspach, Jr. et al. |
| 5,507,754 A | 4/1996 | Green et al. |
| 5,522,845 A | 6/1996 | Wenstrom, Jr. |
| 5,522,899 A | 6/1996 | Michelson |
| 5,531,792 A | 7/1996 | Huene |
| 5,534,004 A | 7/1996 | Santangelo |
| 5,534,029 A | 7/1996 | Shima |
| 5,549,617 A | 8/1996 | Green et al. |
| 5,554,191 A | 9/1996 | Lahille et al. |
| 5,562,689 A | 10/1996 | Green et al. |
| 5,571,104 A | 11/1996 | Li |
| 5,571,109 A | 11/1996 | Bertagnoli |
| 5,571,189 A | 11/1996 | Kuslich |
| 5,578,035 A | 11/1996 | Lin |
| 5,591,168 A | 1/1997 | Judet et al. |
| 5,593,409 A | 1/1997 | Michelson |
| 5,609,635 A | 3/1997 | Michelson |
| 5,609,636 A | 3/1997 | Kohrs et al. |
| 5,613,974 A | 3/1997 | Andreas et al. |
| 5,620,012 A | 4/1997 | Benderev et al. |

(56) References Cited

U.S. PATENT DOCUMENTS

| | | |
|---|---|---|
| 5,643,321 A | 7/1997 | Mcdevitt |
| 5,658,335 A | 8/1997 | Allen |
| 5,683,394 A | 11/1997 | Rinner |
| 5,702,449 A | 12/1997 | Mckay |
| 5,713,899 A | 2/1998 | Marnay et al. |
| 5,741,253 A | 4/1998 | Michelson |
| 5,755,798 A | 5/1998 | Papavero et al. |
| 5,766,252 A | 6/1998 | Henry et al. |
| 5,766,253 A | 6/1998 | Brosnahan, III |
| 5,772,661 A | 6/1998 | Michelson |
| 5,776,199 A | 7/1998 | Michelson |
| 5,782,830 A | 7/1998 | Farris |
| 5,782,919 A | 7/1998 | Zdeblick et al. |
| 5,797,909 A | 8/1998 | Michelson |
| 5,800,547 A | 9/1998 | Schafer et al. |
| 5,800,550 A | 9/1998 | Sertich |
| 5,810,820 A | 9/1998 | Santori et al. |
| 5,849,004 A | 12/1998 | Bramlet |
| 5,860,973 A | 1/1999 | Michelson |
| 5,865,845 A | 2/1999 | Thalgott |
| 5,888,222 A | 3/1999 | Coates et al. |
| 5,888,223 A | 3/1999 | Bray, Jr. |
| 5,888,224 A | 3/1999 | Beckers et al. |
| 5,888,227 A | 3/1999 | Cottle |
| 5,888,228 A | 3/1999 | Knothe et al. |
| 5,895,427 A | 4/1999 | Kuslich et al. |
| 5,968,098 A | 10/1999 | Winslow |
| 5,976,139 A | 11/1999 | Bramlet |
| 5,980,522 A | 11/1999 | Koros et al. |
| 5,984,967 A | 11/1999 | Zdeblick et al. |
| 5,989,289 A | 11/1999 | Coates et al. |
| 6,001,130 A | 12/1999 | Bryan et al. |
| 6,033,438 A | 3/2000 | Bianchi et al. |
| 6,045,552 A | 4/2000 | Zucherman et al. |
| 6,045,579 A | 4/2000 | Hochshuler et al. |
| 6,059,787 A | 5/2000 | Allen |
| 6,063,121 A | 5/2000 | Xavier et al. |
| 6,066,174 A | 5/2000 | Farris |
| 6,066,175 A | 5/2000 | Henderson et al. |
| 6,080,158 A | 6/2000 | Lin |
| 6,080,193 A | 6/2000 | Hochshuler et al. |
| 6,093,205 A | 7/2000 | Mcleod et al. |
| 6,096,038 A | 8/2000 | Michelson |
| 6,096,080 A | 8/2000 | Nicholson et al. |
| 6,099,531 A | 8/2000 | Bonutti |
| 6,102,950 A | 8/2000 | Vaccaro |
| 6,111,164 A | 8/2000 | Rainey et al. |
| 6,113,637 A | 9/2000 | Gill et al. |
| 6,113,638 A | 9/2000 | Williams et al. |
| 6,120,502 A | 9/2000 | Michelson |
| 6,123,705 A | 9/2000 | Michelson |
| 6,129,763 A | 10/2000 | Chauvin et al. |
| 6,136,031 A | 10/2000 | Middleton |
| 6,143,032 A | 11/2000 | Schafer et al. |
| 6,146,421 A | 11/2000 | Gordon et al. |
| 6,149,650 A | 11/2000 | Michelson |
| 6,156,067 A | 12/2000 | Bryan et al. |
| 6,174,311 B1 | 1/2001 | Branch et al. |
| 6,179,873 B1 | 1/2001 | Zientek |
| 6,179,875 B1 | 1/2001 | Von Strempel |
| 6,183,474 B1 | 2/2001 | Bramlet et al. |
| 6,193,757 B1 | 2/2001 | Foley et al. |
| 6,206,922 B1 | 3/2001 | Zdeblick et al. |
| 6,206,923 B1 | 3/2001 | Boyd et al. |
| 6,210,412 B1 | 4/2001 | Michelson |
| 6,210,442 B1 | 4/2001 | Wing et al. |
| 6,214,050 B1 | 4/2001 | Huene |
| 6,224,595 B1 | 5/2001 | Michelson |
| 6,231,610 B1 | 5/2001 | Geisler |
| 6,235,059 B1 | 5/2001 | Benezech et al. |
| 6,241,733 B1 | 6/2001 | Nicholson et al. |
| 6,241,769 B1 | 6/2001 | Nicholson et al. |
| 6,241,770 B1 | 6/2001 | Michelson |
| 6,245,072 B1 | 6/2001 | Zdeblick et al. |
| 6,245,108 B1 | 6/2001 | Biscup |
| 6,251,140 B1 | 6/2001 | Marino et al. |
| 6,258,089 B1 | 7/2001 | Campbell et al. |
| 6,258,094 B1 | 7/2001 | Nicholson et al. |
| 6,258,125 B1 | 7/2001 | Paul et al. |
| 6,261,293 B1 | 7/2001 | Nicholson et al. |
| 6,261,295 B1 | 7/2001 | Nicholson et al. |
| 6,264,656 B1 | 7/2001 | Michelson |
| 6,267,764 B1 | 7/2001 | Elberg |
| 6,270,498 B1 | 8/2001 | Michelson et al. |
| 6,277,149 B1 | 8/2001 | Boyle et al. |
| 6,296,664 B1 | 10/2001 | Middleton |
| 6,302,914 B1 | 10/2001 | Michelson |
| 6,306,170 B2 | 10/2001 | Ray |
| 6,315,797 B1 | 11/2001 | Middleton |
| 6,342,074 B1 | 1/2002 | Simpson |
| 6,344,057 B1 | 2/2002 | Rabbe et al. |
| 6,348,071 B1 | 2/2002 | Steffee et al. |
| 6,350,283 B1 | 2/2002 | Michelson |
| 6,364,880 B1 | 4/2002 | Michelson |
| 6,368,350 B1 | 4/2002 | Erickson et al. |
| 6,371,987 B1 | 4/2002 | Weiland et al. |
| 6,371,988 B1 | 4/2002 | Pafford et al. |
| 6,375,655 B1 | 4/2002 | Zdeblick et al. |
| 6,383,186 B1 | 5/2002 | Michelson |
| 6,395,031 B1 | 5/2002 | Foley et al. |
| 6,395,035 B2 | 5/2002 | Bresina et al. |
| 6,402,750 B1 | 6/2002 | Atkinson et al. |
| 6,402,785 B1 | 6/2002 | Zdeblick et al. |
| 6,409,765 B1 | 6/2002 | Bianchi et al. |
| 6,419,703 B1 | 7/2002 | Fallin et al. |
| 6,419,704 B1 | 7/2002 | Ferree |
| 6,419,706 B1 | 7/2002 | Graf |
| 6,423,063 B1 | 7/2002 | Bonutti |
| 6,423,095 B1 | 7/2002 | Van Hoeck et al. |
| 6,432,106 B1 | 8/2002 | Fraser |
| 6,432,107 B1 | 8/2002 | Ferree |
| 6,447,512 B1 | 9/2002 | Landry et al. |
| 6,447,544 B1 | 9/2002 | Michelson |
| 6,447,546 B1 | 9/2002 | Bramlet et al. |
| 6,447,547 B1 | 9/2002 | Michelson |
| 6,454,769 B2 | 9/2002 | Wagner et al. |
| 6,458,159 B1 | 10/2002 | Thalgott |
| 6,461,359 B1 | 10/2002 | Tribus |
| 6,468,310 B1 | 10/2002 | Ralph et al. |
| 6,471,724 B2 | 10/2002 | Zdeblick et al. |
| 6,478,823 B1 | 11/2002 | Michelson |
| 6,482,233 B1 | 11/2002 | Aebi et al. |
| 6,482,584 B1 | 11/2002 | Mills et al. |
| 6,485,517 B1 | 11/2002 | Michelson |
| 6,497,726 B1 | 12/2002 | Carter et al. |
| 6,500,205 B1 | 12/2002 | Michelson |
| 6,506,216 B1 | 1/2003 | McCue et al. |
| 6,524,312 B2 | 2/2003 | Landry et al. |
| 6,527,803 B1 | 3/2003 | Crozet et al. |
| 6,527,806 B2 | 3/2003 | Ralph et al. |
| 6,540,753 B2 | 4/2003 | Cohen |
| 6,540,785 B1 | 4/2003 | Gill et al. |
| 6,554,863 B2 | 4/2003 | Paul et al. |
| 6,558,423 B1 | 5/2003 | Michelson |
| 6,558,424 B2 | 5/2003 | Thalgott |
| 6,565,605 B2 | 5/2003 | Goble et al. |
| 6,576,016 B1 | 6/2003 | Hochshuler et al. |
| 6,579,291 B1 | 6/2003 | Keith et al. |
| 6,582,468 B1 | 6/2003 | Gauchet |
| 6,592,624 B1 | 7/2003 | Fraser et al. |
| 6,599,320 B1 | 7/2003 | Kuslich |
| 6,605,089 B1 | 8/2003 | Michelson |
| 6,607,530 B1 | 8/2003 | Carl et al. |
| 6,610,065 B1 | 8/2003 | Branch et al. |
| 6,610,089 B1 | 8/2003 | Liu et al. |
| 6,610,092 B2 | 8/2003 | Ralph et al. |
| 6,610,093 B1 | 8/2003 | Pisharodi |
| 6,613,091 B1 | 9/2003 | Zdeblick et al. |
| 6,613,278 B1 | 9/2003 | Mills et al. |
| 6,616,671 B2 | 9/2003 | Landry et al. |
| 6,620,163 B1 | 9/2003 | Michelson |
| 6,635,086 B2 | 10/2003 | Lin |
| 6,635,087 B2 | 10/2003 | Angelucci et al. |
| 6,645,206 B1 | 11/2003 | Zdeblick et al. |

(56) References Cited

U.S. PATENT DOCUMENTS

| | | |
|---|---|---|
| 6,645,249 B2 | 11/2003 | Ralph et al. |
| 6,648,893 B2 | 11/2003 | Dudasik |
| 6,652,584 B2 | 11/2003 | Michelson |
| 6,652,818 B1 | 11/2003 | Mills et al. |
| 6,660,038 B2 | 12/2003 | Boyer, II et al. |
| 6,666,890 B2 | 12/2003 | Michelson |
| 6,669,730 B2 | 12/2003 | Ralph et al. |
| 6,669,731 B2 | 12/2003 | Ralph et al. |
| 6,673,113 B2 | 1/2004 | Ralph et al. |
| 6,676,703 B2 | 1/2004 | Biscup |
| 6,679,887 B2 | 1/2004 | Nicholson et al. |
| 6,679,915 B1 | 1/2004 | Cauthen |
| 6,695,846 B2 | 2/2004 | Richelsoph et al. |
| 6,695,851 B2 | 2/2004 | Zdeblick et al. |
| 6,695,882 B2 | 2/2004 | Bianchi et al. |
| 6,706,067 B2 | 3/2004 | Shimp et al. |
| 6,709,458 B2 | 3/2004 | Michelson |
| 6,712,818 B1 | 3/2004 | Michelson |
| 6,716,247 B2 | 4/2004 | Michelson |
| 6,719,794 B2 | 4/2004 | Gerber et al. |
| 6,723,128 B2 | 4/2004 | Uk |
| 6,733,504 B2 | 5/2004 | Lin et al. |
| 6,733,531 B1 | 5/2004 | Trieu |
| 6,733,535 B2 | 5/2004 | Michelson |
| 6,736,850 B2 | 5/2004 | Davis |
| 6,740,117 B2 | 5/2004 | Ralph et al. |
| 6,740,118 B2 | 5/2004 | Eisermann et al. |
| 6,743,255 B2 | 6/2004 | Ferree |
| 6,743,256 B2 | 6/2004 | Mason |
| 6,743,257 B2 | 6/2004 | Castro |
| 6,749,636 B2 | 6/2004 | Michelson |
| 6,758,849 B1 | 7/2004 | Michelson |
| 6,767,367 B1 | 7/2004 | Michelson |
| 6,770,074 B2 | 8/2004 | Michelson |
| 6,770,096 B2 | 8/2004 | Bolger et al. |
| 6,793,679 B2 | 9/2004 | Michelson |
| RE38,614 E | 10/2004 | Paul et al. |
| 6,800,092 B1 | 10/2004 | Williams et al. |
| 6,800,093 B2 | 10/2004 | Nicholson et al. |
| 6,805,713 B1 | 10/2004 | Carter et al. |
| 6,805,714 B2 | 10/2004 | Sutcliffe |
| 6,808,537 B2 | 10/2004 | Michelson |
| 6,835,206 B2 | 12/2004 | Jackson |
| 6,849,093 B2 | 2/2005 | Michelson |
| 6,890,355 B2 | 5/2005 | Michelson |
| 6,899,735 B2 | 5/2005 | Coates et al. |
| 6,902,580 B2 | 6/2005 | Fallin et al. |
| 6,923,811 B1 | 8/2005 | Carl et al. |
| 6,923,830 B2 | 8/2005 | Michelson |
| 6,936,071 B1 | 8/2005 | Marnay et al. |
| 6,955,691 B2 | 10/2005 | Chae et al. |
| 6,962,606 B2 | 11/2005 | Michelson |
| 6,964,687 B1 | 11/2005 | Bernard et al. |
| 6,972,019 B2 | 12/2005 | Michelson |
| 6,972,035 B2 | 12/2005 | Michelson |
| 6,981,975 B2 | 1/2006 | Michelson |
| 6,984,234 B2 | 1/2006 | Bray |
| 6,994,727 B2 | 2/2006 | Khandkar et al. |
| 7,001,385 B2 | 2/2006 | Bonutti |
| 7,008,453 B1 | 3/2006 | Michelson |
| 7,018,412 B2 | 3/2006 | Ferreira et al. |
| 7,033,394 B2 | 4/2006 | Michelson |
| 7,041,135 B2 | 5/2006 | Michelson |
| 7,041,136 B2 | 5/2006 | Goble et al. |
| 7,048,762 B1 | 5/2006 | Sander et al. |
| 7,048,765 B1 | 5/2006 | Grooms et al. |
| 7,051,610 B2 | 5/2006 | Stoianovici et al. |
| 7,060,097 B2 | 6/2006 | Fraser et al. |
| 7,063,701 B2 | 6/2006 | Michelson |
| 7,063,702 B2 | 6/2006 | Michelson |
| 7,066,961 B2 | 6/2006 | Michelson |
| 7,074,237 B2 | 7/2006 | Goble et al. |
| 7,090,698 B2 | 8/2006 | Goble et al. |
| 7,094,239 B1 | 8/2006 | Michelson |
| 7,112,206 B2 | 9/2006 | Michelson |
| 7,118,579 B2 | 10/2006 | Michelson |
| 7,118,598 B2 | 10/2006 | Michelson |
| 7,128,760 B2 | 10/2006 | Michelson |
| 7,128,761 B2 | 10/2006 | Kuras et al. |
| 7,137,984 B2 | 11/2006 | Michelson |
| 7,153,325 B2 | 12/2006 | Kim et al. |
| 7,163,561 B2 | 1/2007 | Michelson |
| 7,204,852 B2 | 4/2007 | Marnay et al. |
| 7,211,112 B2 | 5/2007 | Baynham et al. |
| 7,217,291 B2 | 5/2007 | Zucherman et al. |
| 7,217,293 B2 | 5/2007 | Branch |
| 7,223,289 B2 | 5/2007 | Trieu et al. |
| 7,232,463 B2 | 6/2007 | Falahee |
| 7,232,464 B2 | 6/2007 | Mathieu |
| 7,235,082 B2 | 6/2007 | Bartish et al. |
| 7,255,698 B2 | 8/2007 | Michelson |
| 7,276,081 B1 | 10/2007 | Coates et al. |
| 7,291,170 B2 | 11/2007 | Huppert |
| 7,303,583 B1 | 12/2007 | Schar Manuel et al. |
| 7,326,248 B2 | 2/2008 | Michelson |
| 7,361,196 B2 | 4/2008 | Fallin et al. |
| 7,410,501 B2 | 8/2008 | Michelson |
| 7,431,735 B2 | 10/2008 | Liu et al. |
| 7,435,262 B2 | 10/2008 | Michelson |
| 7,442,209 B2 | 10/2008 | Michelson |
| 7,445,635 B2 | 11/2008 | Fallin et al. |
| 7,445,636 B2 | 11/2008 | Michelson |
| 7,455,684 B2 | 11/2008 | Gradel et al. |
| 7,455,692 B2 | 11/2008 | Michelson |
| 7,465,317 B2 | 12/2008 | Malberg et al. |
| 7,473,276 B2 | 1/2009 | Aebi et al. |
| 7,479,160 B2 | 1/2009 | Branch et al. |
| 7,503,933 B2 | 3/2009 | Michelson |
| 7,540,882 B2 | 6/2009 | Michelson |
| 7,563,284 B2 | 7/2009 | Coppes et al. |
| 7,563,286 B2 | 7/2009 | Gerber et al. |
| 7,566,345 B1 | 7/2009 | Fallin et al. |
| 7,588,590 B2 | 9/2009 | Chervitz et al. |
| 7,591,851 B2 | 9/2009 | Winslow et al. |
| 7,594,931 B2 | 9/2009 | Louis et al. |
| 7,594,932 B2 | 9/2009 | Aferzon et al. |
| 7,601,170 B2 | 10/2009 | Winslow et al. |
| 7,604,654 B2 | 10/2009 | Fallin et al. |
| 7,608,107 B2 | 10/2009 | Michelson |
| 7,611,538 B2 | 11/2009 | Belliard et al. |
| 7,618,453 B2 | 11/2009 | Goble et al. |
| 7,618,455 B2 | 11/2009 | Goble et al. |
| 7,618,456 B2 | 11/2009 | Mathieu et al. |
| 7,621,955 B2 | 11/2009 | Goble et al. |
| 7,621,958 B2 | 11/2009 | Zdeblick et al. |
| 7,625,393 B2 | 12/2009 | Fallin et al. |
| 7,637,951 B2 | 12/2009 | Michelson |
| 7,637,953 B2 | 12/2009 | Branch et al. |
| 7,637,954 B2 | 12/2009 | Michelson |
| 7,641,690 B2 | 1/2010 | Abdou |
| 7,655,027 B2 | 2/2010 | Michelson |
| 7,658,766 B2 | 2/2010 | Melkent et al. |
| 7,682,396 B2 | 3/2010 | Beaurain et al. |
| 7,695,516 B2 | 4/2010 | Zeegers |
| 7,695,517 B2 | 4/2010 | Benzel et al. |
| 7,727,280 B2 | 6/2010 | McLuen |
| 7,744,602 B2 | 6/2010 | Teeny et al. |
| 7,749,252 B2 | 7/2010 | Zucherman et al. |
| 7,749,274 B2 | 7/2010 | Razian |
| 7,753,937 B2 | 7/2010 | Chervitz et al. |
| 7,771,473 B2 | 8/2010 | Thramann |
| 7,771,475 B2 | 8/2010 | Michelson |
| 7,771,478 B2 | 8/2010 | Navarro et al. |
| 7,776,090 B2 | 8/2010 | Winslow et al. |
| 7,780,670 B2 | 8/2010 | Bonutti |
| 7,789,914 B2 | 9/2010 | Michelson |
| 7,794,502 B2 | 9/2010 | Michelson |
| 7,799,053 B2 | 9/2010 | Haid, Jr. et al. |
| 7,799,057 B2 | 9/2010 | Hudgins et al. |
| 7,799,081 B2 | 9/2010 | McKinley |
| 7,811,326 B2 | 10/2010 | Braddock, Jr. et al. |
| 7,819,903 B2 | 10/2010 | Fraser et al. |
| 7,824,445 B2 | 11/2010 | Biro et al. |
| 7,833,255 B2 | 11/2010 | Chow et al. |

(56) References Cited

U.S. PATENT DOCUMENTS

| | | |
|---|---|---|
| 7,842,088 B2 | 11/2010 | Rashbaum et al. |
| 7,846,188 B2 | 12/2010 | Moskowitz et al. |
| 7,846,207 B2 | 12/2010 | Lechmann et al. |
| 7,850,731 B2 | 12/2010 | Brittan et al. |
| 7,850,732 B2 | 12/2010 | Heinz |
| 7,850,733 B2 | 12/2010 | Baynham et al. |
| 7,862,616 B2 | 1/2011 | Lechmann et al. |
| 7,871,441 B2 | 1/2011 | Eckman |
| 7,875,076 B2 | 1/2011 | Mathieu et al. |
| 7,887,591 B2 | 2/2011 | Aebi et al. |
| 7,892,261 B2 | 2/2011 | Bonutti |
| 7,892,286 B2 | 2/2011 | Michelson |
| 7,905,886 B1 | 3/2011 | Curran et al. |
| 7,909,871 B2 | 3/2011 | Abdou |
| 7,914,560 B2 | 3/2011 | Hoy et al. |
| 7,922,729 B2 | 4/2011 | Michelson |
| 7,931,674 B2 | 4/2011 | Zucherman et al. |
| 7,931,840 B2 | 4/2011 | Michelson |
| 7,935,149 B2 | 5/2011 | Michelson |
| 7,951,198 B2 | 5/2011 | Sucec et al. |
| 7,955,390 B2 | 6/2011 | Fallin et al. |
| 7,972,337 B2 | 7/2011 | Boyajian et al. |
| 7,972,363 B2 | 7/2011 | Moskowitz et al. |
| 7,972,365 B2 | 7/2011 | Michelson |
| 7,976,566 B2 | 7/2011 | Michelson |
| 7,985,255 B2 | 7/2011 | Bray et al. |
| 7,985,258 B2 | 7/2011 | Zdeblick et al. |
| 7,993,373 B2 | 8/2011 | Hoy et al. |
| 7,998,177 B2 | 8/2011 | Hoy et al. |
| 7,998,178 B2 | 8/2011 | Hoy et al. |
| 7,998,211 B2 | 8/2011 | Baccelli et al. |
| 8,007,534 B2 | 8/2011 | Michelson |
| 8,021,401 B2 | 9/2011 | Carl et al. |
| 8,021,430 B2 | 9/2011 | Michelson |
| 8,043,334 B2 | 10/2011 | Fisher et al. |
| 8,062,336 B2 | 11/2011 | Triplett et al. |
| 8,062,375 B2 | 11/2011 | Glerum et al. |
| 8,066,741 B2 | 11/2011 | Fallin et al. |
| 8,066,749 B2 | 11/2011 | Winslow et al. |
| 8,070,816 B2 | 12/2011 | Taylor |
| 8,070,819 B2 | 12/2011 | Aferzon et al. |
| 8,075,593 B2 | 12/2011 | Hess |
| 8,075,618 B2 | 12/2011 | Trieu et al. |
| 8,075,621 B2 | 12/2011 | Michelson |
| 8,080,062 B2 | 12/2011 | Armstrong et al. |
| 8,097,034 B2 | 1/2012 | Michelson |
| 8,114,082 B2 | 2/2012 | Boyajian et al. |
| 8,118,873 B2 | 2/2012 | Humphreys et al. |
| 8,137,405 B2 | 3/2012 | Kostuik et al. |
| 8,147,556 B2 | 4/2012 | Louis et al. |
| 8,167,946 B2 | 5/2012 | Michelson |
| 8,167,949 B2 | 5/2012 | Tyber et al. |
| 8,167,950 B2 | 5/2012 | Aferzon et al. |
| 8,182,539 B2 | 5/2012 | Tyber et al. |
| 8,187,329 B2 | 5/2012 | Theofilos |
| 8,187,332 B2 | 5/2012 | Mcluen |
| 8,216,312 B2 | 7/2012 | Gray |
| 8,241,359 B2 | 8/2012 | Davis et al. |
| 8,257,443 B2 | 9/2012 | Kamran et al. |
| 8,267,999 B2 | 9/2012 | Beaurain et al. |
| 8,303,663 B2 | 11/2012 | Jimenez et al. |
| 8,313,528 B1 | 11/2012 | Wensel |
| 8,323,345 B2 | 12/2012 | Sledge |
| 8,343,197 B2 | 1/2013 | Gonzalez-Hernandez |
| 8,343,219 B2 | 1/2013 | Allain et al. |
| 8,349,015 B2 | 1/2013 | Bae et al. |
| 8,535,352 B2 | 9/2013 | Altarac et al. |
| 8,545,563 B2 | 10/2013 | Brun et al. |
| 8,617,245 B2 | 12/2013 | Brett |
| 8,696,681 B2 | 4/2014 | Harris et al. |
| 8,979,932 B2 | 3/2015 | Rashbaum et al. |
| 9,044,337 B2 | 6/2015 | Dinville et al. |
| 9,173,745 B2 * | 11/2015 | Dinville ............... A61F 2/447 |
| 9,566,164 B2 | 2/2017 | Zeegers |
| 9,763,803 B2 | 9/2017 | Dinville et al. |
| 9,833,331 B2 | 12/2017 | Dinville et al. |
| 2001/0018614 A1 | 8/2001 | Bianchi |
| 2001/0020185 A1 | 9/2001 | Ray |
| 2001/0031254 A1 | 10/2001 | Bianchi et al. |
| 2001/0031967 A1 | 10/2001 | Nicholson et al. |
| 2002/0016592 A1 | 2/2002 | Branch et al. |
| 2002/0026243 A1 | 2/2002 | Lin |
| 2002/0032483 A1 | 3/2002 | Nicholson et al. |
| 2002/0040243 A1 | 4/2002 | Attali et al. |
| 2002/0059938 A1 | 5/2002 | Fogarty et al. |
| 2002/0070565 A1 | 6/2002 | Szapucki et al. |
| 2002/0072806 A1 | 6/2002 | Buskirk et al. |
| 2002/0082597 A1 | 6/2002 | Fraser |
| 2002/0082700 A1 | 6/2002 | Bianchi et al. |
| 2002/0087212 A1 | 7/2002 | James et al. |
| 2002/0106393 A1 | 8/2002 | Bianchi et al. |
| 2002/0107572 A1 | 8/2002 | Foley et al. |
| 2002/0119437 A1 | 8/2002 | Grooms et al. |
| 2002/0138143 A1 | 9/2002 | Grooms et al. |
| 2002/0151893 A1 | 10/2002 | Santilli |
| 2002/0156528 A1 | 10/2002 | Gau |
| 2002/0161444 A1 | 10/2002 | Choi |
| 2002/0165612 A1 | 11/2002 | Gerber et al. |
| 2002/0165613 A1 | 11/2002 | Lin et al. |
| 2002/0193880 A1 | 12/2002 | Fraser |
| 2003/0023304 A1 | 1/2003 | Carter et al. |
| 2003/0027125 A1 | 2/2003 | Mills et al. |
| 2003/0028249 A1 | 2/2003 | Baccelli et al. |
| 2003/0060886 A1 | 3/2003 | Van Hoeck et al. |
| 2003/0069640 A1 | 4/2003 | Ferreira et al. |
| 2003/0074075 A1 | 4/2003 | Thomas, Jr. et al. |
| 2003/0097179 A1 | 5/2003 | Carter et al. |
| 2003/0100950 A1 | 5/2003 | Moret |
| 2003/0109928 A1 | 6/2003 | Pasquet et al. |
| 2003/0135279 A1 | 7/2003 | Michelson |
| 2003/0139815 A1 | 7/2003 | Grooms et al. |
| 2003/0149438 A1 | 8/2003 | Nichols et al. |
| 2003/0149484 A1 | 8/2003 | Michelson |
| 2003/0167091 A1 | 9/2003 | Scharf |
| 2003/0187436 A1 | 10/2003 | Bolger et al. |
| 2003/0191531 A1 | 10/2003 | Berry et al. |
| 2003/0195514 A1 | 10/2003 | Trieu et al. |
| 2003/0195626 A1 | 10/2003 | Huppert |
| 2003/0195629 A1 | 10/2003 | Pafford et al. |
| 2003/0195632 A1 | 10/2003 | Foley et al. |
| 2003/0204260 A1 | 10/2003 | Ferree |
| 2003/0233147 A1 | 12/2003 | Nicholson et al. |
| 2004/0010312 A1 | 1/2004 | Enayati |
| 2004/0030387 A1 | 2/2004 | Landry et al. |
| 2004/0073307 A1 | 4/2004 | Keller |
| 2004/0073309 A1 | 4/2004 | Bianchi et al. |
| 2004/0073313 A1 | 4/2004 | Link et al. |
| 2004/0093083 A1 | 5/2004 | Branch et al. |
| 2004/0097929 A1 | 5/2004 | Branch et al. |
| 2004/0115172 A1 | 6/2004 | Bianchi et al. |
| 2004/0117022 A1 | 6/2004 | Marnay et al. |
| 2004/0127990 A1 | 7/2004 | Bartish, Jr. et al. |
| 2004/0127993 A1 | 7/2004 | Kast et al. |
| 2004/0127994 A1 | 7/2004 | Kast et al. |
| 2004/0143332 A1 | 7/2004 | Krueger et al. |
| 2004/0148028 A1* | 7/2004 | Ferree ................ A61F 2/4425 623/17.11 |
| 2004/0148029 A1 | 7/2004 | Bianchi et al. |
| 2004/0153157 A1 | 8/2004 | Keller |
| 2004/0162617 A1 | 8/2004 | Zucherman et al. |
| 2004/0172020 A1 | 9/2004 | Beaurain et al. |
| 2004/0172130 A1 | 9/2004 | Nakahara et al. |
| 2004/0199254 A1 | 10/2004 | Louis et al. |
| 2004/0210219 A1 | 10/2004 | Bray |
| 2004/0210308 A1 | 10/2004 | Carter et al. |
| 2004/0210313 A1 | 10/2004 | Michelson |
| 2004/0230306 A1 | 11/2004 | Hoeck et al. |
| 2004/0243238 A1 | 12/2004 | Arnin et al. |
| 2004/0243240 A1 | 12/2004 | Beaurain et al. |
| 2004/0254577 A1 | 12/2004 | Delecrin et al. |
| 2004/0254643 A1 | 12/2004 | Jackson |
| 2005/0004672 A1 | 1/2005 | Pafford et al. |
| 2005/0010215 A1 | 1/2005 | Delecrin et al. |
| 2005/0015149 A1 | 1/2005 | Michelson |

(56) References Cited

U.S. PATENT DOCUMENTS

| | | |
|---|---|---|
| 2005/0027359 A1 | 2/2005 | Mashburn |
| 2005/0027360 A1 | 2/2005 | Webb et al. |
| 2005/0027362 A1 | 2/2005 | Williams et al. |
| 2005/0038511 A1 | 2/2005 | Martz et al. |
| 2005/0038512 A1 | 2/2005 | Michelson |
| 2005/0049590 A1 | 3/2005 | Alleyne et al. |
| 2005/0060034 A1 | 3/2005 | Berry et al. |
| 2005/0060037 A1 | 3/2005 | Michelson |
| 2005/0065608 A1 | 3/2005 | Michelson |
| 2005/0065611 A1 | 3/2005 | Huppert et al. |
| 2005/0085917 A1 | 4/2005 | Marnay et al. |
| 2005/0096742 A1 | 5/2005 | Mills et al. |
| 2005/0096745 A1 | 5/2005 | Andre et al. |
| 2005/0100862 A1 | 5/2005 | Mills et al. |
| 2005/0101957 A1 | 5/2005 | Buskirk et al. |
| 2005/0107788 A1 | 5/2005 | Beaurain et al. |
| 2005/0119744 A1 | 6/2005 | Buskirk et al. |
| 2005/0119747 A1 | 6/2005 | Fabris Monterumici et al. |
| 2005/0143733 A1 | 6/2005 | Petit |
| 2005/0143825 A1 | 6/2005 | Enayati |
| 2005/0149189 A1 | 7/2005 | Mokhtar et al. |
| 2005/0165483 A1 | 7/2005 | Ray et al. |
| 2005/0171554 A1 | 8/2005 | Estes et al. |
| 2005/0197706 A1 | 9/2005 | Hovorka et al. |
| 2005/0246024 A1 | 11/2005 | Zeegers |
| 2005/0283236 A1 | 12/2005 | Razian |
| 2005/0288788 A1 | 12/2005 | Dougherty-Shah |
| 2006/0058878 A1 | 3/2006 | Michelson |
| 2006/0069437 A1 | 3/2006 | Weber |
| 2006/0085071 A1 | 4/2006 | Lechmann et al. |
| 2006/0085076 A1 | 4/2006 | Krishna et al. |
| 2006/0089717 A1 | 4/2006 | Krishna et al. |
| 2006/0095136 A1 | 5/2006 | Mcluen |
| 2006/0121084 A1 | 6/2006 | Borden et al. |
| 2006/0122703 A1 | 6/2006 | Aebi et al. |
| 2006/0129244 A1 | 6/2006 | Ensign |
| 2006/0136063 A1 | 6/2006 | Zeegers |
| 2006/0142863 A1 | 6/2006 | Fraser et al. |
| 2006/0155377 A1 | 7/2006 | Beaurain et al. |
| 2006/0173544 A1 | 8/2006 | Gau |
| 2006/0186063 A1 | 8/2006 | Campbell |
| 2006/0206208 A1 | 9/2006 | Michelson |
| 2006/0235426 A1 | 10/2006 | Lim et al. |
| 2006/0241621 A1 | 10/2006 | Moskowitz et al. |
| 2006/0241761 A1 | 10/2006 | Gately |
| 2006/0241764 A1 | 10/2006 | Michelson |
| 2006/0253201 A1 | 11/2006 | Mcluen |
| 2006/0276899 A1 | 12/2006 | Zipnick et al. |
| 2006/0282074 A1 | 12/2006 | Renaud et al. |
| 2007/0016217 A1 | 1/2007 | Dinville |
| 2007/0016297 A1 | 1/2007 | Johnson |
| 2007/0032871 A1 | 2/2007 | Michelson |
| 2007/0049943 A1 | 3/2007 | Moskowitz et al. |
| 2007/0073404 A1 | 3/2007 | Rashbaum et al. |
| 2007/0093850 A1 | 4/2007 | Harris et al. |
| 2007/0106388 A1 | 5/2007 | Michelson |
| 2007/0142843 A1 | 6/2007 | Dye |
| 2007/0149974 A1 | 6/2007 | Mangione |
| 2007/0162128 A1 | 7/2007 | DeRidder et al. |
| 2007/0162130 A1 | 7/2007 | Rashbaum et al. |
| 2007/0179623 A1 | 8/2007 | Trieu et al. |
| 2007/0208345 A1 | 9/2007 | Marnay et al. |
| 2007/0250167 A1 | 10/2007 | Bray et al. |
| 2007/0260249 A1 | 11/2007 | Boyajian et al. |
| 2007/0270951 A1 | 11/2007 | Davis et al. |
| 2007/0270954 A1 | 11/2007 | Wu |
| 2007/0270960 A1 | 11/2007 | Bonin, Jr. et al. |
| 2007/0270961 A1 | 11/2007 | Ferguson |
| 2007/0270967 A1 | 11/2007 | Fallin et al. |
| 2007/0276498 A1 | 11/2007 | Aebi et al. |
| 2008/0021562 A1 | 1/2008 | Huppert |
| 2008/0027547 A1 | 1/2008 | Yu et al. |
| 2008/0027550 A1 | 1/2008 | Link et al. |
| 2008/0033432 A1 | 2/2008 | Mcgraw et al. |
| 2008/0033562 A1 | 2/2008 | Krishna et al. |
| 2008/0051887 A1 | 2/2008 | Carter et al. |
| 2008/0109083 A1 | 5/2008 | Van Hoeck et al. |
| 2008/0125865 A1 | 5/2008 | Abdelgany |
| 2008/0132949 A1 | 6/2008 | Aferzon et al. |
| 2008/0161933 A1 | 7/2008 | Grotz et al. |
| 2008/0177306 A1 | 7/2008 | Lamborne et al. |
| 2008/0195211 A1 | 8/2008 | Lin et al. |
| 2008/0200984 A1 | 8/2008 | Jodaitis et al. |
| 2008/0234686 A1 | 9/2008 | Beaurain et al. |
| 2008/0249569 A1 | 10/2008 | Waugh et al. |
| 2008/0249575 A1 | 10/2008 | Waugh et al. |
| 2008/0249625 A1 | 10/2008 | Waugh et al. |
| 2008/0281425 A1 | 11/2008 | Thalgott et al. |
| 2008/0294260 A1 | 11/2008 | Gray |
| 2008/0300634 A1 | 12/2008 | Gray |
| 2008/0300685 A1 | 12/2008 | Carls et al. |
| 2008/0306596 A1 | 12/2008 | Jones et al. |
| 2008/0312743 A1 | 12/2008 | Vila et al. |
| 2009/0030461 A1 | 1/2009 | Hoy et al. |
| 2009/0030519 A1 | 1/2009 | Falahee |
| 2009/0030520 A1 | 1/2009 | Biedermann et al. |
| 2009/0099601 A1 | 4/2009 | Aferzon et al. |
| 2009/0099604 A1 | 4/2009 | Cho et al. |
| 2009/0105830 A1 | 4/2009 | Jones et al. |
| 2009/0105831 A1 | 4/2009 | Jones et al. |
| 2009/0105832 A1 | 4/2009 | Allain et al. |
| 2009/0112271 A1 | 4/2009 | Moskowitz et al. |
| 2009/0118771 A1 | 5/2009 | Gonzalez-Hernandez |
| 2009/0125071 A1 | 5/2009 | Skinlo et al. |
| 2009/0132054 A1 | 5/2009 | Zeegers |
| 2009/0157188 A1 | 6/2009 | Zeegers |
| 2009/0164020 A1 | 6/2009 | Janowski et al. |
| 2009/0182381 A1 | 7/2009 | Beaurain et al. |
| 2009/0182429 A1 | 7/2009 | Humphreys et al. |
| 2009/0182430 A1 | 7/2009 | Tyber et al. |
| 2009/0186333 A1 | 7/2009 | Mills et al. |
| 2009/0192613 A1 | 7/2009 | Wing et al. |
| 2009/0192615 A1 | 7/2009 | Tyber et al. |
| 2009/0204219 A1 | 8/2009 | Beaurain et al. |
| 2009/0210062 A1 | 8/2009 | Thalgott et al. |
| 2009/0216241 A1 | 8/2009 | Dinville |
| 2009/0216331 A1 | 8/2009 | Grotz et al. |
| 2009/0222092 A1 | 9/2009 | Davis et al. |
| 2009/0222100 A1 | 9/2009 | Cipoletti et al. |
| 2009/0228108 A1 | 9/2009 | Keller |
| 2009/0234455 A1 | 9/2009 | Moskowitz et al. |
| 2009/0265007 A1 | 10/2009 | Colleran |
| 2009/0270990 A1 | 10/2009 | Louis et al. |
| 2010/0004664 A1 | 1/2010 | Boyajian et al. |
| 2010/0016903 A1 | 1/2010 | Matityahu et al. |
| 2010/0016974 A1 | 1/2010 | Janowski et al. |
| 2010/0049259 A1 | 2/2010 | Lambrecht et al. |
| 2010/0050276 A1 | 2/2010 | Depaepe |
| 2010/0057206 A1 | 3/2010 | Duffield et al. |
| 2010/0057207 A1 | 3/2010 | Ray, III et al. |
| 2010/0063554 A1 | 3/2010 | Branch et al. |
| 2010/0070037 A1 | 3/2010 | Parry et al. |
| 2010/0082104 A1 | 4/2010 | Carter et al. |
| 2010/0082109 A1 | 4/2010 | Greenhalgh et al. |
| 2010/0087925 A1 | 4/2010 | Kostuik et al. |
| 2010/0106249 A1 | 4/2010 | Tyber et al. |
| 2010/0114317 A1 | 5/2010 | Lambrecht et al. |
| 2010/0121455 A1 | 5/2010 | Lambrecht et al. |
| 2010/0145459 A1 | 6/2010 | Mcdonough et al. |
| 2010/0145460 A1 | 6/2010 | McDonough et al. |
| 2010/0145463 A1 | 6/2010 | Michelson |
| 2010/0152856 A1 | 6/2010 | Overes et al. |
| 2010/0160984 A1 | 6/2010 | Berry et al. |
| 2010/0161057 A1 | 6/2010 | Berry et al. |
| 2010/0179655 A1 | 7/2010 | Hansell et al. |
| 2010/0185289 A1 | 7/2010 | Kirwan et al. |
| 2010/0204796 A1 | 8/2010 | Bae et al. |
| 2010/0211108 A1 | 8/2010 | Lemole, Jr. |
| 2010/0211176 A1 | 8/2010 | Greenhalgh |
| 2010/0217393 A1 | 8/2010 | Theofilos |
| 2010/0217396 A1 | 8/2010 | Bianchi et al. |
| 2010/0234958 A1 | 9/2010 | Linares |
| 2010/0249935 A1 | 9/2010 | Slivka et al. |
| 2010/0249937 A1 | 9/2010 | Blain et al. |

(56) References Cited

U.S. PATENT DOCUMENTS

| | | |
|---|---|---|
| 2010/0268349 A1 | 10/2010 | Bianchi et al. |
| 2010/0280618 A1 | 11/2010 | Jodaitis et al. |
| 2010/0286777 A1 | 11/2010 | Errico et al. |
| 2010/0286787 A1 | 11/2010 | Villiers et al. |
| 2010/0298941 A1 | 11/2010 | Hes et al. |
| 2010/0305700 A1 | 12/2010 | Ben-arye et al. |
| 2010/0305704 A1 | 12/2010 | Messerli et al. |
| 2010/0312344 A1 | 12/2010 | Reiley |
| 2010/0312345 A1 | 12/2010 | Duffield et al. |
| 2010/0312346 A1 | 12/2010 | Kueenzi et al. |
| 2011/0004310 A1 | 1/2011 | Michelson |
| 2011/0009966 A1 | 1/2011 | Michelson |
| 2011/0015745 A1 | 1/2011 | Bucci |
| 2011/0035007 A1 | 2/2011 | Patel et al. |
| 2011/0040382 A1 | 2/2011 | Muhanna |
| 2011/0054616 A1 | 3/2011 | Kamran et al. |
| 2011/0077738 A1 | 3/2011 | Ciupik et al. |
| 2011/0077739 A1 | 3/2011 | Rashbaum et al. |
| 2011/0082553 A1 | 4/2011 | Abdou |
| 2011/0087327 A1 | 4/2011 | Lechmann et al. |
| 2011/0093077 A1 | 4/2011 | Aebi et al. |
| 2011/0098747 A1 | 4/2011 | Donner et al. |
| 2011/0112587 A1 | 5/2011 | Patel et al. |
| 2011/0118843 A1 | 5/2011 | Mathieu et al. |
| 2011/0125267 A1 | 5/2011 | Michelson |
| 2011/0137420 A1 | 6/2011 | Michelson |
| 2011/0144703 A1 | 6/2011 | Krause et al. |
| 2011/0160860 A1 | 6/2011 | Johnston et al. |
| 2011/0166655 A1 | 7/2011 | Michelson |
| 2011/0166656 A1 | 7/2011 | Thalgott et al. |
| 2011/0166657 A1 | 7/2011 | Thalgott et al. |
| 2011/0166658 A1 | 7/2011 | Garber et al. |
| 2011/0172774 A1 | 7/2011 | Varela |
| 2011/0178599 A1 | 7/2011 | Brett |
| 2011/0196492 A1 | 8/2011 | Lambrecht et al. |
| 2011/0196493 A1 | 8/2011 | Pimenta |
| 2011/0196494 A1 | 8/2011 | Yedlicka et al. |
| 2011/0202136 A1 | 8/2011 | Brittan et al. |
| 2011/0208311 A1 | 8/2011 | Janowski |
| 2011/0208313 A1 | 8/2011 | Michelson |
| 2011/0230969 A1 | 9/2011 | Biedermann et al. |
| 2011/0230971 A1 | 9/2011 | Donner et al. |
| 2011/0264227 A1 | 10/2011 | Boyajian et al. |
| 2011/0295371 A1 | 12/2011 | Moskowitz et al. |
| 2011/0301707 A1 | 12/2011 | Buskirk et al. |
| 2011/0301713 A1 | 12/2011 | Theofilos |
| 2011/0301714 A1 | 12/2011 | Theofilos |
| 2011/0313528 A1 | 12/2011 | Laubert et al. |
| 2012/0004660 A1 | 1/2012 | Grooms et al. |
| 2012/0022654 A1 | 1/2012 | Farris et al. |
| 2012/0053693 A1 | 3/2012 | Zeegers |
| 2012/0078371 A1 | 3/2012 | Gamache et al. |
| 2012/0116466 A1 | 5/2012 | Dinville et al. |
| 2012/0191196 A1 | 7/2012 | Louis et al. |
| 2012/0197404 A1 | 8/2012 | Brun et al. |
| 2012/0265248 A1 | 10/2012 | Delecrin et al. |
| 2012/0310356 A1 | 12/2012 | Davis et al. |
| 2012/0330424 A1 | 12/2012 | Zeegers |
| 2013/0013006 A1 | 1/2013 | Rashbaum et al. |
| 2013/0041408 A1 | 2/2013 | Dinville et al. |
| 2013/0123926 A1 | 5/2013 | Bae et al. |
| 2013/0150968 A1 | 6/2013 | Dinville et al. |
| 2013/0166029 A1 | 6/2013 | Dinville et al. |
| 2013/0226300 A1 | 8/2013 | Chataigner et al. |
| 2013/0253648 A1 | 9/2013 | Beaurain et al. |
| 2013/0253651 A1 | 9/2013 | Dinville |
| 2013/0282124 A1 | 10/2013 | Jodaitis et al. |
| 2014/0052262 A1 | 2/2014 | Brett |
| 2014/0114413 A1 | 4/2014 | Allain et al. |
| 2014/0121778 A1 | 5/2014 | Huppert |
| 2014/0135932 A1 | 5/2014 | Davis et al. |
| 2014/0135935 A1 | 5/2014 | Vila et al. |
| 2014/0148855 A1 | 5/2014 | Beaurain et al. |
| 2014/0214168 A1 | 7/2014 | Jodaitis et al. |
| 2014/0228885 A1 | 8/2014 | Dinville et al. |
| 2014/0316466 A1 | 10/2014 | Dinville et al. |
| 2014/0364949 A1 | 12/2014 | Beaurain et al. |
| 2015/0025638 A1 | 1/2015 | Rashbaum et al. |
| 2015/0032209 A1 | 1/2015 | Hovorka et al. |
| 2015/0045893 A1 | 2/2015 | Dinville et al. |
| 2015/0051702 A1 | 2/2015 | Chataigner et al. |
| 2015/0080959 A1 | 3/2015 | Renaud et al. |
| 2015/0127107 A1 | 5/2015 | Kim et al. |
| 2015/0127109 A1 | 5/2015 | Brett |
| 2015/0182259 A1 | 7/2015 | Cho et al. |
| 2015/0182264 A1 | 7/2015 | Delecrin et al. |
| 2015/0190240 A1 | 7/2015 | Rashbaum et al. |
| 2015/0209089 A1 | 7/2015 | Chataigner et al. |
| 2015/0245918 A1 | 9/2015 | Zeegers |
| 2015/0250605 A1 | 9/2015 | Chataigner et al. |
| 2015/0257895 A1 | 9/2015 | Zeegers |
| 2015/0257896 A1 | 9/2015 | Dinville et al. |
| 2015/0320568 A1 | 11/2015 | Ameil et al. |
| 2016/0008142 A1 | 1/2016 | Louis et al. |
| 2016/0100870 A1 | 4/2016 | Lavigne et al. |
| 2016/0100953 A1 | 4/2016 | Dinville et al. |
| 2016/0220389 A1 | 8/2016 | Dinville |
| 2017/0042692 A1 | 2/2017 | Stewart et al. |
| 2018/0092753 A1 | 4/2018 | Dinville et al. |
| 2018/0161173 A1 | 6/2018 | Dinville et al. |

FOREIGN PATENT DOCUMENTS

| | | |
|---|---|---|
| AU | 2016203916 B2 | 1/2018 |
| AU | 2017279684 A1 | 1/2018 |
| DE | 3741493 A1 | 6/1989 |
| DE | 4327054 C1 | 4/1995 |
| DE | 20320454 U1 | 10/2004 |
| DE | 10323363 A1 | 12/2004 |
| EP | 0637439 A1 | 2/1995 |
| EP | 0667127 A1 | 8/1995 |
| EP | 0697200 A1 | 2/1996 |
| EP | 0951879 A2 | 10/1999 |
| EP | 0965313 A1 | 12/1999 |
| EP | 2113228 A1 | 11/2009 |
| EP | 2327375 A1 | 6/2011 |
| EP | 2340788 A1 | 7/2011 |
| EP | 2363080 A1 | 9/2011 |
| EP | 2389902 A1 | 11/2011 |
| EP | 2519194 A1 | 11/2012 |
| EP | 2519194 B1 | 1/2018 |
| EP | 3323390 A1 | 5/2018 |
| FR | 2703580 A1 | 10/1994 |
| FR | 2733413 A1 | 10/1996 |
| FR | 2747034 A1 | 10/1997 |
| FR | 2808995 A1 | 11/2001 |
| FR | 2823095 A1 | 10/2002 |
| FR | 2827156 A1 | 1/2003 |
| FR | 2846550 A1 | 5/2004 |
| FR | 2861582 A1 | 5/2005 |
| FR | 2879436 A1 | 6/2006 |
| FR | 2880795 A1 | 7/2006 |
| FR | 2891135 A1 | 3/2007 |
| FR | 2897259 A1 | 8/2007 |
| FR | 2916956 A1 | 12/2008 |
| FR | 2987256 A1 | 8/2013 |
| FR | 3005569 A1 | 11/2014 |
| FR | 3016793 A1 | 7/2015 |
| RU | 2004218 C1 | 12/1993 |
| WO | WO-9508306 A1 | 3/1995 |
| WO | WO-9715248 A1 | 5/1997 |
| WO | WO-9801091 A1 | 1/1998 |
| WO | WO-9855052 A1 | 12/1998 |
| WO | WO-9909914 A1 | 3/1999 |
| WO | WO-9956676 A1 | 11/1999 |
| WO | WO-9963914 A1 | 12/1999 |
| WO | WO-0024327 A2 | 5/2000 |
| WO | WO-0101894 A1 | 1/2001 |
| WO | WO-0170141 A1 | 9/2001 |
| WO | WO-0187194 A1 | 11/2001 |
| WO | WO-0213732 A2 | 2/2002 |
| WO | WO-02013732 A2 | 2/2002 |
| WO | WO-02058599 A2 | 8/2002 |
| WO | WO-02089701 A2 | 11/2002 |

(56) References Cited

FOREIGN PATENT DOCUMENTS

| WO | WO-03005939 A2 | 1/2003 | | |
|---|---|---|---|---|
| WO | WO-2004034935 A1 | 4/2004 | | |
| WO | WO-2004041129 A1 | 5/2004 | | |
| WO | WO-2004080356 A2 | 9/2004 | | |
| WO | WO-2004089256 A1 | 10/2004 | | |
| WO | WO-2006047587 A2 | 5/2006 | | |
| WO | WO-2006102269 A2 | 9/2006 | | |
| WO | WO-2006120505 A1 | 11/2006 | | |
| WO | WO-2007078978 A2 | 7/2007 | | |
| WO | WO-2007093900 A2 | 8/2007 | | |
| WO | WO-2008044057 A1 | 4/2008 | | |
| WO | WO 2008149223 A2 * | 12/2008 | ......... | A61B 17/0642 |
| WO | WO-2009033100 A1 | 3/2009 | | |
| WO | WO-2010090801 A2 | 8/2010 | | |
| WO | WO 2011056845 A1 * | 5/2011 | ......... | A61B 17/1671 |
| WO | WO-2011080535 A1 | 7/2011 | | |
| WO | WO-2011129973 A1 | 10/2011 | | |
| WO | WO-2013124453 A1 | 8/2013 | | |
| WO | WO-2014184367 A1 | 11/2014 | | |
| WO | WO-2015114122 A1 | 8/2015 | | |

OTHER PUBLICATIONS

"U.S. Appl. No. 10/276,712, Final Office Action dated Nov. 14, 2005", 7 pgs.
"U.S. Appl. No. 10/276,712, Final Office Action dated Dec. 20, 2006", 7 pgs.
"U.S. Appl. No. 10/276,712, Final Office Action dated Dec. 23, 2004", 6 pgs.
"U.S. Appl. No. 10/276,712, Non Final Office Action dated May 27, 2005", 7 pgs.
"U.S. Appl. No. 10/276,712, Non Final Office Action dated Jun. 7, 2006", 7 pgs.
"U.S. Appl. No. 10/276,712, Non Final Office Action dated Jun. 30, 2004", 9 pgs.
"U.S. Appl. No. 10/276,712, Notice of Allowance dated Jul. 30, 2007", 4 pgs.
"U.S. Appl. No. 10/276,712, Response filed Jan. 17, 2006 to Final Office Action dated Nov. 14, 2005", 9 pgs.
"U.S. Appl. No. 10/276,712, Response filed Mar. 1, 2005 to Final Office Action dated Dec. 23, 2004", 10 pgs.
"U.S. Appl. No. 10/276,712, Response filed Mar. 14, 2006 to Advisory Action dated Feb. 8, 2006", 8 pgs.
"U.S. Appl. No. 10/276,712, Response filed Jun. 19, 2007 to Final Office Action dated Dec. 20, 2006", 10 pgs.
"U.S. Appl. No. 10/276,712, Response filed Aug. 29, 2005 to Non Final Office Action dated May 27, 2005", 12 pgs.
"U.S. Appl. No. 10/276,712, Response filed Sep. 27, 2004 to Non Final Office Action dated Jun. 30, 2004", 12 pgs.
"U.S. Appl. No. 10/276,712, Response filed Oct. 6, 2006 to Non Final Office Action dated Jun. 7, 2006", 12 pgs.
"U.S. Appl. No. 10/483,563, Corrected Notice of Allowance dated Jun. 19, 2009", 4 pgs.
"U.S. Appl. No. 10/483,563, Final Office Action dated Oct. 28, 2008", 9 pgs.
"U.S. Appl. No. 10/483,563, Non Final Office Action dated Jun. 31, 2008", 8 pgs.
"U.S. Appl. No. 10/483,563, Non Final Office Action dated Feb. 21, 2007", 6 pgs.
"U.S. Appl. No. 10/483,563, Non Final Office Action dated Oct. 30, 2007", 6 pgs.
"U.S. Appl. No. 10/483,563, Notice of Allowance dated Jun. 5, 2009", 4 pgs.
"U.S. Appl. No. 10/483,563, Response filed Apr. 28, 2009 to Final Office Action dated Oct. 28, 2008", 8 pgs.
"U.S. Appl. No. 10/483,563, Response filed Jul. 31, 2008 to Non Final Office Action dated Jan. 31, 2008", 13 pgs.
"U.S. Appl. No. 10/483,563, Response filed Aug. 21, 2007 to Non Final Office Action dated Feb. 21, 2007", 12 pgs.
"U.S. Appl. No. 10/483,563, Response filed Nov. 19, 2007 to Non Final Office Action dated Oct. 30, 2007", 4 pgs.
"U.S. Appl. No. 10/533,846, Final Office Action dated Oct. 15, 2008", 13 pgs.
"U.S. Appl. No. 10/533,846, Non Final Office Action dated Apr. 18, 2007", 11 pgs.
"U.S. Appl. No. 10/533,846, Non Final Office Action dated Dec. 26, 2007", 14 pgs.
"U.S. Appl. No. 10/533,846, Notice of Allowance dated Nov. 4, 2009", 4 pgs.
"U.S. Appl. No. 10/533,846, Response filed Apr. 15, 2009 to Final Office Action dated Oct. 15, 2008", 13 pgs.
"U.S. Appl. No. 10/533,846, Response filed Jun. 25, 2008 to Non Final Office Action dated Dec. 26, 2007", 18 pgs.
"U.S. Appl. No. 10/533,846, Response filed Oct. 16, 2007 to Non Final Office Action dated Apr. 18, 2007", 16 pgs.
"U.S. Appl. No. 11/109,276, Final Office Action dated Jul. 24, 2008", 12 pgs.
"U.S. Appl. No. 11/109,276, Non Final Office Action dated Feb. 6, 2007", 12 pgs.
"U.S. Appl. No. 11/109,276, Non Final Office Action dated Feb. 13, 2009", 5 pgs.
"U.S. Appl. No. 11/109,276, Non Final Office Action dated Oct. 16, 2007", 12 pgs.
"U.S. Appl. No. 11/109,276, Notice of Allowance dated Dec. 8, 2009", 8 pgs.
"U.S. Appl. No. 11/109,276, Response filed Jan. 26, 2009 to Final Office Action dated Jul. 24, 2008", 9 pgs.
"U.S. Appl. No. 11/109,276, Response filed Apr. 16, 2008 to Non Final Office Action dated Oct. 16, 2007", 16 pgs.
"U.S. Appl. No. 11/109,276, Response filed Aug. 4, 2009 to Non Final Office Action dated Feb. 13, 2009", 8 pgs.
"U.S. Appl. No. 11/109,276, Response filed Aug. 6, 2007 to Non Final Office Action dated Feb. 6, 2007", 39 pgs.
"U.S. Appl. No. 11/341,007, Final Office Action dated Dec. 17, 2009", 17 pgs.
"U.S. Appl. No. 11/341,007, Non Final Office Action dated Apr. 13, 2009", 13 pgs.
"U.S. Appl. No. 11/341,007, Notice of Allowance dated Jul. 26, 2010", 6 pgs.
"U.S. Appl. No. 11/341,007, Response filed Jun. 17, 2010 to Final Office Action dated Dec. 17, 2009", 12 pgs.
"U.S. Appl. No. 11/341,007, Response filed Oct. 13, 2009 to Non Final Office Action dated Apr. 13, 2009", 15 pgs.
"U.S. Appl. No. 11/378,165, Advisory Action dated Aug. 11, 2009", 3 pgs.
"U.S. Appl. No. 11/378,165, Applicant's Summary of Examiner Interview filed Feb. 26, 2013", 3 pgs.
"U.S. Appl. No. 11/378,165, Applicant's Summary of Examiner Interview filed Jun. 18, 2010", 1 pg.
"U.S. Appl. No. 11/378,165, Examiner Interview Summary dated May 20, 2010", 3 pgs.
"U.S. Appl. No. 11/378,165, Final Office Action dated Feb. 17, 2009", 16 pgs.
"U.S. Appl. No. 11/378,165, Final Office Action dated Sep. 24, 2010", 18 pgs.
"U.S. Appl. No. 11/378,165, Non Final Office Action dated May 27, 2008", 15 pgs.
"U.S. Appl. No. 11/378,165, Non Final Office Action dated Jun. 4, 2012", 27 pgs.
"U.S. Appl. No. 11/378,165, Non Final Office Action dated Oct. 26, 2009", 24 pgs.
"U.S. Appl. No. 11/378,165, Notice of Allowance dated Nov. 26, 2012", 10 pgs.
"U.S. Appl. No. 11/378,165, Response filed Feb. 28, 2008 to Restriction Requirement dated Sep. 28, 2007", 12 pgs.
"U.S. Appl. No. 11/378,165, Response filed Mar. 24, 2011 to Final Office Action dated Sep. 24, 2010", 15 pgs.
"U.S. Appl. No. 11/378,165, Response filed Apr. 26, 2010 to Non Final Office Action dated Oct. 26, 2009", 12 pgs.
"U.S. Appl. No. 11/378,165, Response filed Aug. 4, 2009 to Final Office Action dated Feb. 17, 2009", 14 pgs.

(56) References Cited

OTHER PUBLICATIONS

"U.S. Appl. No. 11/378,165, Response filed Nov. 5, 2012 to Non Final Office Action dated Jun. 4, 2012", 14 pgs.
"U.S. Appl. No. 11/378,165, Response filed Nov. 26, 2008 to Non Final Office Action dated May 27, 2008", 5 pgs.
"U.S. Appl. No. 11/378,165, Restriction Requirement dated Sep. 28, 2007", 9 pgs.
"U.S. Appl. No. 11/767,386, Final Office Action dated Mar. 24, 2011", 11 pgs.
"U.S. Appl. No. 11/767,386, Non Final Office Action dated Apr. 24, 2013", 10 pgs.
"U.S. Appl. No. 11/767,386, Non Final Office Action dated Jul. 21, 2010", 10 pgs.
"U.S. Appl. No. 11/767,386, Notice of Allowance dated Aug. 30, 2013", 6 pgs.
"U.S. Appl. No. 11/767,386, Response filed Jan. 21, 2011 to Non Final Office Action dated Jul. 21, 2010", 21 pgs.
"U.S. Appl. No. 11/767,386, Response filed Apr. 26, 2010 to Restriction Requirement dated Dec. 24, 2009", 9 pgs.
"U.S. Appl. No. 11/767,386, Response filed Jul. 24, 2013 to Non Final Office Action dated Apr. 24, 2013", 14 pgs.
"U.S. Appl. No. 11/767,386, Response filed Sep. 26, 2011 to Final Office Action dated Mar. 24, 2011", 18 pgs.
"U.S. Appl. No. 11/767,386, Restriction Requirement dated Dec. 24, 2009", 5 pgs.
"U.S. Appl. No. 12/134,884, Non Final Office Action dated Jan. 31, 2012", 7 pgs.
"U.S. Appl. No. 12/134,884, Notice of Allowance dated Nov. 1, 2012", 7 pgs.
"U.S. Appl. No. 12/134,884, Response filed Jul. 31, 2012 to Non Final Office Action dated Jan. 31, 2012", 20 pgs.
"U.S. Appl. No. 12/279,664, Non Final Office Action dated Sep. 14, 2011", 13 pgs.
"U.S. Appl. No. 12/279,664, Notice of Allowance dated Apr. 11, 2012", 11 pgs.
"U.S. Appl. No. 12/279,664, Notice of Allowance dated May 29, 2012", 4 pgs.
"U.S. Appl. No. 12/279,664, Response filed Mar. 14, 2012 to Non Final Office Action dated Sep. 14, 2011", 21 pgs.
"U.S. Appl. No. 12/360,050, Non Final Office Action dated Sep. 6, 2011", 11 pgs.
"U.S. Appl. No. 12/360,050, Non Final Office Action dated Dec. 17, 2010", 14 pgs.
"U.S. Appl. No. 12/360,050, Notice of Allowance dated Mar. 26, 2012", 5 pgs.
"U.S. Appl. No. 12/360,050, Notice of Allowance dated May 18, 2012", 4 pgs.
"U.S. Appl. No. 12/360,050, Notice of Allowance dated Jul. 6, 2012", 5 pgs.
"U.S. Appl. No. 12/360,050, Notice of Allowance dated Aug. 2, 2012", 2 pgs.
"U.S. Appl. No. 12/360,050, Response filed Mar. 6, 2012 to Non Final Office Action dated Sep. 6, 2011", 14 pgs.
"U.S. Appl. No. 12/360,050, Response filed Jun. 16, 2011 to Non Final Office Action dated Dec. 17, 2010", 34 pgs.
"U.S. Appl. No. 12/424,136, Response filed May 18, 2011 to Final Office Action dated Mar. 18, 2011", 7 pgs.
"U.S. Appl. No. 12/424,364, Applicant's Summary of Examiner Interview filed May 22, 2012", 3 pgs.
"U.S. Appl. No. 12/424,364, Non Final Office Action dated Jan. 26, 2012", 10 pgs.
"U.S. Appl. No. 12/424,364, Non Final Office Action dated May 18, 2011", 10 pgs.
"U.S. Appl. No. 12/424,364, Non Final Office Action dated May 23, 2012", 6 pgs.
"U.S. Appl. No. 12/424,364, Notice of Allowance dated Jul. 24, 2012", 5 pgs.
"U.S. Appl. No. 12/424,364, Notice of Allowance dated Aug. 2, 2012", 2 pgs.
"U.S. Appl. No. 12/424,364, Response filed Feb. 27, 2012 to Non Final Office Action dated Jan. 26, 2012", 6 pgs.
"U.S. Appl. No. 12/424,364, Response filed Jul. 6, 2012 to Non Final Office Action dated May 23, 2012", 4 pgs.
"U.S. Appl. No. 12/424,364, Response filed Nov. 18, 2011 to Non Final Office Action dated May 18, 2011", 13 pgs.
"U.S. Appl. No. 12/430,768, Corrected Notice of Allowance dated Jan. 19, 2012", 2 pgs.
"U.S. Appl. No. 12/430,768, Non Final Office Action dated Jun. 14, 2011", 7 pgs.
"U.S. Appl. No. 12/430,768, Notice of Allowance dated Jan. 11, 2012", 5 pgs.
"U.S. Appl. No. 12/430,768, Response filed Dec. 14, 2011 to Non Final Office Action dated Jun. 14, 2011", 7 pgs.
"U.S. Appl. No. 12/884,664, Examiner Interview Summary dated Dec. 18, 2012", 2 pgs.
"U.S. Appl. No. 12/884,664, Non Final Office Action dated Jan. 15, 2013", 7 pgs.
"U.S. Appl. No. 12/884,664, Notice of Allowance dated Aug. 6, 2013", 9 pgs.
"U.S. Appl. No. 12/884,664, Response filed Apr. 10, 2013 to Non Final Office Action dated Jan. 15, 2013", 16 pgs.
"U.S. Appl. No. 12/884,664, Response filed Oct. 16, 2012 to Restriction Requirement dated Sep. 26, 2012", 15 pgs.
"U.S. Appl. No. 12/884,664, Restriction Requirement dated Sep. 26, 2012", 6 pgs.
"U.S. Appl. No. 12/955,898, Final Office Action dated Jan. 10, 2013", 17 pgs.
"U.S. Appl. No. 12/955,898, Non Final Office Action dated Mar. 3, 2014", 11 pgs.
"U.S. Appl. No. 12/955,898, Non Final Office Action dated Jun. 1, 2012", 27 pgs.
"U.S. Appl. No. 12/955,898, Notice of Allowance dated Jan. 29, 2015", 7 pgs.
"U.S. Appl. No. 12/955,898, Notice of Allowance dated Aug. 8, 2014", 7 pgs.
"U.S. Appl. No. 12/955,898, Response filed Apr. 19, 2012 to Restriction Requirement dated Mar. 19, 2012", 11 pgs.
"U.S. Appl. No. 12/955,898, Response filed Jul. 10, 2013 to Final Office Action dated Jan. 10, 2013", 12 pgs.
"U.S. Appl. No. 12/955,898, Response filed Aug. 4, 2014 to Non Final Office Action dated Mar. 3, 2014", 11 pgs.
"U.S. Appl. No. 12/955,898, Response filed Dec. 3, 2012 to Non Final Office Action dated Jun. 1, 2012", 20 pgs.
"U.S. Appl. No. 12/955,898, Restriction Requirement dated Mar. 19, 2012", 9 pgs.
"U.S. Appl. No. 13/158,761, Examiner Interview Summary dated Aug. 1, 2013", 3 pgs.
"U.S. Appl. No. 13/158,761, Examiner Interview Summary dated Oct. 31, 2012", 3 pgs.
"U.S. Appl. No. 13/158,761, Final Office Action dated Aug. 14, 2013", 11 pgs.
"U.S. Appl. No. 13/158,761, Final Office Action dated Oct. 22, 2014", 12 pgs.
"U.S. Appl. No. 13/158,761, Non Final Office Action dated Feb. 28, 2013", 10 pgs.
"U.S. Appl. No. 13/158,761, Notice of Allowance dated May 12, 2015", 5 pgs.
"U.S. Appl. No. 13/158,761, Notice of Allowance dated Sep. 2, 2015", 5 pgs.
"U.S. Appl. No. 13/158,761, Response filed Apr. 22, 2015 to Final Office Action dated Oct. 22, 2014", 10 pgs.
"U.S. Appl. No. 13/158,761, Response filed Jul. 29, 2013 to Non Final Office Action dated Feb. 28, 2013", 12 pgs.
"U.S. Appl. No. 13/158,761, Response filed Nov. 14, 2013 to Final Office Action dated Aug. 14, 2013", 12 pgs.
"U.S. Appl. No. 13/158,761, Response filed Nov. 19, 2012 to Restriction Requirement dated Oct. 17, 2012", 8 pgs.
"U.S. Appl. No. 13/158,761, Restriction Requirement dated Oct. 17, 2012", 6 pgs.
"U.S. Appl. No. 13/158,761, Supplemental Notice of Allowability dated Sep. 25, 2015", 2 pgs.

(56) References Cited

OTHER PUBLICATIONS

"U.S. Appl. No. 13/438,352, Non Final Office Action dated Aug. 14, 2014", 8 pgs.
"U.S. Appl. No. 13/438,352, Notice of Allowance dated Mar. 2, 2015", 7 pgs.
"U.S. Appl. No. 13/438,352, Response filed Jan. 14, 2015 to Non Final Office Action dated Aug. 14, 2014", 10 pgs.
"U.S. Appl. No. 13/520,041, 312 Amendment filed Jun. 7, 2016", 11 pgs.
"U.S. Appl. No. 13/520,041, Final Office Action dated Mar. 31, 2017", 7 pgs.
"U.S. Appl. No. 13/520,041, Final Office Action dated Oct. 6, 2014", 10 pgs.
"U.S. Appl. No. 13/520,041, Non Final Office Action dated Mar. 20, 2014", 9 pgs.
"U.S. Appl. No. 13/520,041, Non Final Office Action dated Apr. 10, 2015", 7 pgs.
"U.S. Appl. No. 13/520,041, Non Final Office Action dated Aug. 29, 2016", 8 pgs.
"U.S. Appl. No. 13/520,041, Notice of Allowance dated Mar. 8, 2016", 5 pgs.
"U.S. Appl. No. 13/520,041, Notice of Allowance dated Jul. 24, 2017", 5 pgs.
"U.S. Appl. No. 13/520,041, Notice of Allowance dated Nov. 18, 2015", 5 pgs.
"U.S. Appl. No. 13/520,041, Preliminary Amendment filed Jun. 29, 2012", 8 pgs.
"U.S. Appl. No. 13/520,041, Response filed Mar. 6, 2015 to Final Office Action dated Oct. 6, 2014", 12 pgs.
"U.S. Appl. No. 13/520,041, Response filed Jun. 30, 2017 to Final Office Action dated Mar. 31, 2017", 13 pgs.
"U.S. Appl. No. 13/520,041, Response filed Aug. 10, 2015 to Non Final Office Action dated Apr. 10, 2015", 11 pgs.
"U.S. Appl. No. 13/520,041, Response filed Sep. 19, 2014 to Non Final Office Action dated Mar. 20, 2014", 5 pgs.
"U.S. Appl. No. 13/520,041, Response filed Nov. 29, 2016 to Non Final Office Action dated Aug. 29, 2016", 12 pgs.
"U.S. Appl. No. 13/538,078, Non Final Office Action dated May 12, 2014", 12 pgs.
"U.S. Appl. No. 13/538,078, Notice of Allowance dated Oct. 20, 2014", 5 pgs.
"U.S. Appl. No. 13/538,078, Response filed Oct. 14, 2014 to Non Final Office Action dated May 12, 2014", 10 pgs.
"U.S. Appl. No. 13/585,063, Final Office Action dated Nov. 4, 2015", 17 pgs.
"U.S. Appl. No. 13/585,063, Non Final Office Action dated Feb. 11, 2015", 13 pgs.
"U.S. Appl. No. 13/585,063, Response filed Jan. 6, 2015 to Restriction Requirement dated Nov. 6, 2014", 9 pgs.
"U.S. Appl. No. 13/585,063, Response filed Feb. 4, 2016 to Final Office Action dated Nov. 4, 2015", 9 pgs.
"U.S. Appl. No. 13/585,063, Response filed Aug. 11, 2015 to Non Final Office Action dated Feb. 11, 2015", 14 pgs.
"U.S. Appl. No. 13/585,063, Restriction Requirement dated Nov. 6, 2014", 8 pgs.
"U.S. Appl. No. 13/585,063, Supplemental Amendment filed May 4, 2016", 11 pgs.
"U.S. Appl. No. 13/603,043, Final Office Action dated Jul. 24, 2014", 11 pgs.
"U.S. Appl. No. 13/603,043, Non Final Office Action dated Apr. 9, 013", 13 pgs.
"U.S. Appl. No. 13/603,043, Non Final Office Action dated Nov. 21, 2013", 11 pgs.
"U.S. Appl. No. 13/603,043, Notice of Allowance dated Feb. 10, 2015", 5 pgs.
"U.S. Appl. No. 13/603,043, Response filed May 21, 2014 to Non Final Office Action dated Nov. 21, 2013", 13 pgs.
"U.S. Appl. No. 13/603,043, Response filed Oct. 9, 2013 to Non Final Office Action dated Apr. 9, 2013", 37 pgs.
"U.S. Appl. No. 13/603,043, Response filed Dec. 24, 2014 to Final Office Action dated Jul. 24, 2014", 11 pgs.
"U.S. Appl. No. 13/616,448, Non Final Office Action dated Aug. 22, 2013", 6 pgs.
"U.S. Appl. No. 13/616,448, Notice of Allowance dated Feb. 7, 2014", 5 pgs.
"U.S. Appl. No. 13/616,448, Notice of Allowance dated Apr. 21, 2014", 2 pgs.
"U.S. Appl. No. 13/616,448, Response filed Dec. 23, 2013 to Non Final Office Action dated Aug. 22, 2013", 9 pgs.
"U.S. Appl. No. 13/732,244, Final Office Action dated Feb. 20, 2015", 9 pgs.
"U.S. Appl. No. 13/732,244, Final Office Action dated Jun. 8, 2016", 7 pgs.
"U.S. Appl. No. 13/732,244, Non Final Office Action dated Sep. 19, 2014", 4 pgs.
"U.S. Appl. No. 13/732,244, Non Final Office Action dated Oct. 20, 2015", 6 pgs.
"U.S. Appl. No. 13/732,244, Response filed Jan. 20, 2015 to Non Final Office Action dated Sep. 19, 2014", 12 pgs.
"U.S. Appl. No. 13/732,244, Response filed Jan. 20, 2016 to Non Final Office Action dated Oct. 20, 2015", 16 pgs.
"U.S. Appl. No. 13/732,244, Response filed Jul. 30, 2014 to Restriction Requirement dated Apr. 30, 2014", 4 pgs.
"U.S. Appl. No. 13/732,244, Response filed Aug. 20, 2015 to Final Office Action dated Feb. 20, 2015", 13 pgs.
"U.S. Appl. No. 13/732,244, Restriction Requirement dated Apr. 30, 2014", 5 pgs.
"U.S. Appl. No. 13/774,547, Notice of Allowance dated Feb. 2, 2015", 5 pgs.
"U.S. Appl. No. 13/774,547, Notice of Allowance dated Jul. 3, 2014", 12 pgs.
"U.S. Appl. No. 13/774,547, Notice of Allowance dated Oct. 16, 2014", 8 pgs.
"U.S. Appl. No. 13/854,801, Advisory Action dated Nov. 27, 2015", 3 pgs.
"U.S. Appl. No. 13/854,808, Examiner Interview Summary dated Mar. 30, 2016", 3 pgs.
"U.S. Appl. No. 13/854,808, Final Office Action dated Jan. 23, 2015", 16 pgs.
"U.S. Appl. No. 13/854,808, Final Office Action dated Mar. 22, 2016", 10 pgs.
"U.S. Appl. No. 13/854,808, Non Final Office Action dated Jul. 7, 2014", 12 pgs.
"U.S. Appl. No. 13/854,808, Response filed Jan. 7, 2015 to Non Final Office Action dated Jul. 7, 2014", 12 pgs.
"U.S. Appl. No. 13/854,808, Response filed Feb. 29, 2016 to Non Final Office Action dated Nov. 27, 2015", 13 pgs.
"U.S. Appl. No. 13/854,808, Response filed Jun. 18, 2014 to Restriction Requirement dated Apr. 18, 2014", 9 pgs.
"U.S. Appl. No. 13/854,808, Response filed Jul. 23, 2015 to Final Office Action dated Jan. 23, 2015", 12 pgs.
"U.S. Appl. No. 13/854,808, Restriction Requirement dated Apr. 18, 2014", 9 pgs.
"U.S. Appl. No. 14/064,434, Non Final Office Action dated May 5, 2014", 7 pgs.
"U.S. Appl. No. 14/064,434, Notice of Allowance dated Sep. 8, 2014", 5 pgs.
"U.S. Appl. No. 14/064,434, Response filed Apr. 14, 2014 to Restriction Requirement dated Jan. 13, 2014", 21 pgs.
"U.S. Appl. No. 14/064,434, Response filed Aug. 27, 2014 to Non Final Office Action dated May 5, 2014", 12 pgs.
"U.S. Appl. No. 14/064,434, Restriction Requirement dated Jan. 13, 2014", 6 pgs.
"U.S. Appl. No. 14/149,223, Non Final Office Action dated Feb. 10, 2016", 8 pgs.
"U.S. Appl. No. 14/149,357, Advisory Action dated Jun. 1, 2016", 3 pgs.
"U.S. Appl. No. 14/149,357, Final Office Action dated Feb. 10, 2016", 13 pgs.
"U.S. Appl. No. 14/149,357, Non Final Office Action dated Sep. 11, 2015", 10 pgs.

(56) References Cited

OTHER PUBLICATIONS

"U.S. Appl. No. 14/149,357, Response filed May 10, 2016 to Final Office Action dated Feb. 10, 2016", 20 pgs.
"U.S. Appl. No. 14/149,357, Response filed Aug. 31, 2015 to Restriction Requirement dated Jun. 30, 2015", 10 pgs.
"U.S. Appl. No. 14/149,357, Response filed Dec. 11, 2015 to Non Final Office Action dated Sep. 11, 2015", 16 pgs.
"U.S. Appl. No. 14/149,357, Restriction Requirement dated Jun. 30, 2015", 6 pgs.
"U.S. Appl. No. 14/306,785, Final Office Action dated Jun. 22, 2015", 9 pgs.
"U.S. Appl. No. 14/306,785, Non Final Office Action dated Oct. 22, 2014", 6 pgs.
"U.S. Appl. No. 14/306,785, Notice of Allowance dated Oct. 13, 2015", 6 pgs.
"U.S. Appl. No. 14/306,785, Response filed Apr. 22, 2015 to Non Final Office Action dated Oct. 22, 2014", 9 pgs.
"U.S. Appl. No. 14/306,785, Response filed Sep. 22, 2015 to Final Office Action dated Jun. 22, 2015", 11 pgs.
"U.S. Appl. No. 14/594,770, Non Final Office Action dated Jan. 27, 2016", 8 pgs.
"U.S. Appl. No. 14/594,770, Response filed Apr. 27, 2016 to Non Final Office Action dated Jan. 27, 2016", 14 pgs.
"U.S. Appl. No. 14/594,770, Response filed Nov. 2, 2015 to Restriction Requirement dated Jul. 1, 2015", 11 pgs.
"U.S. Appl. No. 14/594,770, Restriction Requirement dated Jul. 1, 2015", 6 pgs.
"U.S. Appl. No. 14/659,587, Non Final Office Action dated Jan. 28, 2016", 10 pgs.
"U.S. Appl. No. 14/659,587, Non Final Office Action dated Apr. 16, 2015", 12 pgs.
"U.S. Appl. No. 14/659,587, Notice of Allowance dated Oct. 9, 2015", 6 pgs.
"U.S. Appl. No. 14/659,587, Response filed Apr. 28, 2016 to Non Final Office Action dated Jan. 28, 2016", 14 pgs.
"U.S. Appl. No. 14/659,587, Response filed Sep. 16, 2015 to Non Final Office Action dated Apr. 16, 2015", 13 pgs.
"U.S. Appl. No. 14/721,818, Advisory Action dated Jun. 1, 2016", 3 pgs.
"U.S. Appl. No. 14/721,818, Final Office Action dated Feb. 1, 2016", 19 pgs.
"U.S. Appl. No. 14/721,818, Non Final Office Action dated Sep. 24, 2015", 21 pgs.
"U.S. Appl. No. 14/721,818, Response filed May 2, 2016 to Final Office Action dated Feb. 1, 2016", 13 pgs.
"U.S. Appl. No. 14/721,818, Response filed Dec. 28, 2015 to Non Final Office Action dated Sep. 24, 2015", 15 pgs.
"U.S. Appl. No. 14/726,557, Non Final Office Action dated Dec. 30, 2015", 12 pgs.
"U.S. Appl. No. 14/726,557, Response filed May 2, 2016 to Non Final Office Action dated Dec. 30, 2015", 33 pgs.
"U.S. Appl. No. 14/726,558, Applicant's Summary of Examiner Interview filed Aug. 18, 2017", 3 pgs.
"U.S. Appl. No. 14/726,558, Final Office Action dated Jan. 5, 2017", 14 pgs.
"U.S. Appl. No. 14/726,558, Non Final Office Action dated Jun. 22, 2016", 13 pgs.
"U.S. Appl. No. 14/726,558, Notice of Allowance dated May 18, 2017", 10 pgs.
"U.S. Appl. No. 14/726,558, Response filed Apr. 5, 2017 to Final Office Action dated Jan. 5, 2017", 12 pgs.
"U.S. Appl. No. 14/726,558, Response filed Oct. 24, 2016 to Non Final Office Action dated Jun. 22, 2016", 11 pgs.
"U.S. Appl. No. 15/708,860, Non Final Office Action dated Apr. 25, 2018", 12 pgs.
"U.S. Appl. No. 15/708,860, Response filed Jul. 25, 2018 to Non Final Office Action dated Apr. 25, 2018", 11 pgs.
"Australian Application Serial No. 2009357504, First Examination Report dated Jun. 10, 2015", 4 pgs.

"Australian Application Serial No. 2016203916, First Examination Report dated Oct. 19, 2016", 3 pgs.
"Canadian Application Serial No. 2,785,617, Office Action dated Mar. 10, 2017", 3 pgs.
"Canadian Application Serial No. 2,785,617, Office Action dated Jul. 8, 2016", 3 pgs.
"Canadian Application Serial No. 2,785,617, Office Action dated Aug. 6, 2015", 3 pgs.
"Canadian Application Serial No. 2,785,617, Office Action dated Sep. 30, 2014", 2 pgs.
"Canadian Application Serial No. 2,785,617, Response filed Jan. 9, 2017 to Office Action dated Jul. 8, 2016", 10 pgs.
"Canadian Application Serial No. 2,785,617, Response filed Feb. 8, 2016 to Office Action dated Aug. 6, 2015", 11 pgs.
"Canadian Application Serial No. 2,785,617, Response filed Mar. 30, 2015 to Office Action dated Sep. 30, 2014", 9 pgs.
"Canadian Application Serial No. 2,785,617, Response filed Sep. 8, 2017 to Office Action dated Mar. 10, 2017", 8 pgs.
"Chinese Application Serial No. 2010848337, Office Action dated Mar. 28, 2014".
"European Application Serial No. 02784881.1, Intention to Grant dated Aug. 26, 2010", 24 pgs.
"European Application Serial No. 02784881.1, Office Action dated Mar. 13, 2009", 2 pgs.
"European Application No. 02784881.1, Office Action dated Aug. 4, 2009", 3 pgs.
"European Application No. 02784881.1, Response filed Jul. 22, 2009 to Office Action dated Mar. 13, 2009", 21 pgs.
"European Application Serial No. 02784881.1, Response filed Oct. 14, 2009 to Office Action dated Aug. 4, 2009", 20 pgs.
"European Application Serial No. 05857774.3, Communication Pursuant to Article 94(3) EPC dated Apr. 11, 2011", 4 pgs.
"European Application Serial No. 05857774.3, Communication Pursuant to Article 94(3) EPC dated May 6, 2009", 3 pgs.
"European Application Serial No. 05857774.3, Response filed Oct. 11, 2011 to Communication Pursuant to Article 94(3) EPC dated Apr. 11, 2011", 20 pgs.
"European Application Serial No. 05857774.3, Response filed Nov. 13, 2009 to Communication Pursuant to Article 94(3) EPC dated May 6, 2009", 22 pgs.
"European Application Serial No. 07733892.9, Response filed Nov. 26, 2008 to Communication pursuant to Rules 161(1) and 162 EPC dated Oct. 27, 2008", 16 pgs.
"European Application Serial No. 08762820.2, Amendment filed Jan. 6, 2010", 23 pgs.
"European Application Serial No. 08762820.2, Communication Pursuant to Article 94(3) EPC dated Jan. 17, 2012", 4 pgs.
"European Application Serial No. 08762820.2, Response filed Jul. 27, 2012 to Communication Pursuant to Article 94(3) EPC dated Jan. 17, 2012", 23 pgs.
"European Application Serial No. 09009533.2, Extended European Search Report dated Oct. 6, 2009", 4 pgs.
"European Application Serial No. 09009533.2, Response filed Apr. 26, 2010 to Extended European Search Report dated Oct. 6, 2009", 10 pgs.
"European Application Serial No. 09812464.7, Communication Pursuant to Article 94(3) EPC dated Mar. 3, 2016", 6 pgs.
"European Application Serial No. 09812464.7, Intention to grant dated Jul. 31, 2017", 6 pgs.
"European Application Serial No. 09812464.7, Response filed Mar. 25, 2013 to Communication Pursuant to Rules 161(1) and 162 EPC dated Sep. 25, 2012", 30 pgs.
"European Application Serial No. 09812464.7, Response filed May 12, 2017 to Summons to Attend Oral Proceedings dated Mar. 1, 2017", 13 pgs.
"European Application Serial No. 09812464.7, Response filed Sep. 12, 2016 to Communication Pursuant to Article 94(3) EPC dated Mar. 3, 2016", 22 pgs.
"European Application Serial No. 09812464.7, Summons to Attend Oral Proceedings dated Mar. 1, 2017", 11 pgs.
"European Application Serial No. 10185004.8, Extended European Search Report dated Apr. 6, 2011", 6 pgs.

(56) References Cited

OTHER PUBLICATIONS

"European Application Serial No. 10759773.4, Office Action dated Oct. 9, 2014", 4 pgs.
"European Application Serial No. 11157596.5, Extended European Search Report dated Jun. 8, 2011", 5 pgs.
"European Application Serial No. 11165170.9, Communication Pursuant to Article 94(3) EPC dated May 15, 2012", 5 pgs.
"European Application Serial No. 11165170.9, Extended European Search Report dated Jul. 21, 2011", 7 pgs.
"European Application Serial No. 11165170.9, Response filed Mar. 6, 2012 to Extended European Search Report dated Jul. 21, 2011", 17 pgs.
"European Application Serial No. 13170071.8, Extended European Search Report dated Oct. 1, 2013", 6 pgs.
"European Application Serial No. 15200239, European Search Report dated Apr. 27, 2016".
"European Application Serial No. 17206736.5, Extended European Search Report dated Mar. 27, 2018", 9 pgs.
"France Application Serial No. 0006351, Search Report dated Jan. 29, 2001", 1 pg.
"France Application Serial No. 0109381, Search Report dated Apr. 5, 2002", 2 pgs.
"France Application Serial No. 0213833, Preliminary Search Report dated Jul. 10, 2003", 2 pgs.
"France Application Serial No. 0413728, Preliminary Search Report dated Aug. 11, 2005", 2 pgs.
"France Application Serial No. 0509740, Preliminary Search Report dated Jun. 27, 2006", 2 pgs.
"France Application Serial No. 0601315, Search Report dated Oct. 11, 2006", 2 pgs.
"France Application Serial No. 0704155, Preliminary Search Report dated Jan. 30, 2008", 3 pgs.
"France Application Serial No. 1251733, Search Report dated Dec. 5, 2012", 2 pgs.
"France Application Serial No. 1354421, Search Report dated Feb. 12, 2014", 5 pgs.
"France Application Serial No. 1450749, Search Report dated Sep. 11, 2014", 2 pgs.
"France Application Serial No. 2891135, Preliminary Search Report dated Jun. 27, 2006", 2 pgs.
"France Application Serial No. 2897259, Search Report dated Oct. 11, 2006".
"France Application Serial No. 2916956, Preliminary Search Report dated Jan. 30, 2008", 3 pgs.
"International Application Serial No. PCT/EP2013/053622, International Preliminary Report on Patentability dated Jul. 11, 2014", 4 pgs.
"International Application Serial No. PCT/EP2013/053622, International Search Report dated May 29, 2013", 3 pgs.
"International Application Serial No. PCT/EP2013/053622, Written Opinion dated May 29, 2013", 3 pgs.
"International Application Serial No. PCT/EP2014/060135, International Search Report dated Aug. 26, 2014", 7 pgs.
"International Application Serial No. PCT/EP2015/052019, International Search Report dated May 13, 2015", 4 pgs.
"International Application Serial No. PCT/EP2015/052019, Written Opinion dated May 13, 2015", 9 pgs.
"International Application Serial No. PCT/FR2001/001545, International Preliminary Examination Report dated Aug. 30, 2002", 16 pgs.
"International Application Serial No. PCT/FR2001/001545, International Search Report dated Sep. 5, 2001", 3 pgs.
"International Application Serial No. PCT/IB2002/003390, International Preliminary Examination Report dated Nov. 6, 2003", 4 pgs.
"International Application Serial No. PCT/IB2002/003390, International Search Report dated Mar. 3, 2003", 2 pgs.
"International Application Serial No. PCT/IB2003/004872, International Preliminary Examination Report dated Mar. 1, 2005", 6 pgs.
"International Application Serial No. PCT/IB2003/004872, International Search Report dated Mar. 3, 2004", 3 pgs.
"International Application Serial No. PCT/IB2005/004093, International Preliminary Report on Patentability dated Feb. 22, 2007", 8 pgs.
"International Application Serial No. PCT/IB2005/004093, International Search Report dated Aug. 31, 2006", 3 pgs.
"International Application Serial No. PCT/IB2005/004093, Written Opinion dated Aug. 31, 2006", 5 pgs.
"International Application Serial No. PCT/IB2006/002632, International Preliminary Report on Patentability dated Aug. 14, 2007", 5 pgs.
"International Application Serial No. PCT/IB2006/002632, International Search Report dated Feb. 23, 2007", 3 pgs.
"International Application Serial No. PCT/IB2006/002632, Written Opinion dated Feb. 23, 2007", 5 pgs.
"International Application Serial No. PCT/IB2007/000367, International Preliminary Report on Patentability dated Feb. 5, 2008", 9 pgs.
"International Application Serial No. PCT/IB2007/000367, International Search Report dated Oct. 22, 2007", 5 pgs.
"International Application Serial No. PCT/IB2007/000367, Written Opinion dated Oct. 22, 2007", 9 pgs.
"International Application Serial No. PCT/IB2008/001484, International Preliminary Report on Patentability dated Aug. 5, 2009", 6 pgs.
"International Application Serial No. PCT/IB2008/001484, International Search Report dated Feb. 16, 2009", 5 pgs.
"International Application Serial No. PCT/IB2008/001484, Written Opinion dated Feb. 16, 2009", 8 pgs.
"International Application Serial No. PCT/IB2009/008048, International Preliminary Report on Patentability dated Apr. 18, 2012", 20 pgs.
"International Application Serial No. PCT/IB2009/008048, International Search Report dated Feb. 2, 2011", 6 pgs.
"International Application Serial No. PCT/IB2009/008048, Written Opinion dated Feb. 2, 2011", 15 pgs.
"International Application Serial No. PCT/US2010/049287, International Preliminary Report on Patentability dated Mar. 29, 2012", 7 pgs.
"International Application Serial No. PCT/US2010/049287, International Search Report dated Jan. 11, 2011", 5 pgs.
"International Application Serial No. PCT/US2010/049287, Written Opinion dated Jan. 11, 2011",5 pgs.
"Japanese Application Serial No. 20080554874, Office Action dated Nov. 4, 2011".
"Japanese Application Serial No. 20080554874, Response filed May 15, 2012 to Office Action dated Nov. 4, 2011".
"Japanese Application Serial No. 2012529931, Office Action dated Jun. 2, 2014".
"Japanese Application Serial No. 20150009322, Office Action dated Dec. 1, 2015".
"LDR Medical, by its attorneys; Chapter II amendments for PCT Pub'n. No. WO2006120505", App. No. PCT/IB2005/004093; Oct. 30, 2006; WIPO, 14 pgs.
"LDR Medical; Greffe et fusion", LDR Medical; France, (Sep. 19, 2004), 1 pg.
"LDR Medical; ROI Privilegier la greffe en creant la chambre de fusion", LDR Medical, (Sep. 19, 2004), 1 pg.
"Mc+ Le choix de l'ancrage", LDR Medical, (Sep. 19, 2004), 1 pg.
"Reply to Office Action in U.S. Appl. No. 13/774,547; dated Feb. 2, 2015", USPTO; Alexandria, Virgina, 6 pgs.

* cited by examiner

INSTRUMENTS AND METHODS FOR REMOVING FIXATION DEVICES FROM INTERVERTEBRAL IMPLANTS

CROSS-REFERENCE TO RELATED APPLICATIONS

This application is a continuation of U.S. patent application Ser. No. 13/158,761 filed Jun. 13, 2011, and issuing as U.S. Pat. No. 9,173,745 on Nov. 3, 2015, which is a continuation in part of International Application No. PCT/IB2009/008048 filed Dec. 31, 2009, in accordance with the Patent Cooperation Treaty and entering the National Stage in the United States as U.S. patent application Ser. No. 13/520,041 with a 35 U.S.C. § 371(c) date of Nov. 26, 2012, each of which is incorporated herein by reference.

BACKGROUND

This disclosure concerns orthopedic implants, including spinal implants such as intervertebral prostheses and intersomatic cages, for example. In particular, this disclosure is directed to devices and methods for removing fixation devices, such as anchors, pins, staples, screws, nails, etc., that have been used to affix an intervertebral implant to one or more adjacent spinal elements.

A healthy intervertebral disc is flexible enough to allow movement between a vertebra and another adjacent spinal column element, such as another vertebra, the coccyx, or the sacrum. This movement accommodates bending of the spine. Disease, degeneration, or injury of the tissues of a natural intervertebral disc often leads to intense pain and reduced spinal mobility. When disease, degeneration, or injury of the natural intervertebral disc has progressed to the point where non-operative care such as medication, injections, and/or physical therapy is ineffective, surgical intervention may be required.

A common procedure for treatment of diseased, degenerated, or injured intervertebral discs involves removal of the natural tissues of the disc and fusion of the adjacent vertebrae. Although fusion eliminates the mobility between the adjacent vertebrae, often it is the preferred method of treatment of disc degeneration or injury.

Intervertebral disc prostheses have been developed to treat diseased, degenerated, or injured intervertebral discs and still provide a relatively normal range of movement to the adjacent vertebra, resulting in a more normal distribution of stresses and movements along the various segments of the spine. Intervertebral disc prostheses typically are configured to restore normal disc height, and can decrease surgical morbidity and complications from postoperative immobilization instrumentation that may be present in fusion procedures.

One problem in this field concerns the stability of spinal implants in the disc space once they have been implanted. For example, there is a risk that the implant will shift in the intervertebral space due to forces imposed when the patient moves, even when the implant is provided with notches or teeth on its vertebral contact surfaces. Therefore, it is often necessary to affix the spinal implant to the adjacent vertebrae during implantation. A number of solutions are known to affix the spinal implant to the adjacent vertebrae using a bone anchoring device, such as an anchor, pin, nail, screw, staple, and other mechanical fixation structures. International Application No. PCT/IB2009/008048 filed Dec. 31, 2009, by the assignee of the present application describes various particularly advantageous fixation devices, instruments, and methods.

Access to the intervertebral spaces often is particularly delicate due to the dimensions involved and the presence of blood vessels and nerves in the approach to the intervertebral space. Bone anchoring devices should have sufficient size, strength, and positioning to ensure good fixation, but preferably the configuration of the anchoring devices, installation tools, and fixation methods allows fixation of the implant without endangering the surrounding blood vessels and nerves. International Application No. PCT/IB2009/008048, for example, describes various advantageous devices, instruments, and methods that reduce the space required in the approach to the intervertebral location compared to conventional devices and methods.

In an ideal outcome, the placement an intervertebral implant will be permanent, and withdrawal of the implant or modification of its position never will be needed. In practice, though, circumstance can arise which indicate that an intervertebral implant should be removed or reposition following the initial fixation to the adjacent vertebral structures. This disclosure describes various structures and steps that may be useful for removing or repositioning an implant after its initial fixation.

SUMMARY OF THE DISCLOSURE

Various embodiments of anchor removal instruments and methods for using the instruments are described. In some embodiments, an intervertebral implant anchor extractor tool comprises a support, a support retainer configured to hold the support fixed with respect to the implant, an extractor having an anchor retainer, and an extractor guide. An embodiment of a method of using this implant anchor extractor tool comprises the steps of obtaining access to an anchor, grasping the anchor, and applying a withdrawal force on the anchor while applying a countervailing force against the implant or a vertebral structure.

DETAILED DESCRIPTION OF VARIOUS EMBODIMENTS

Figure 1:
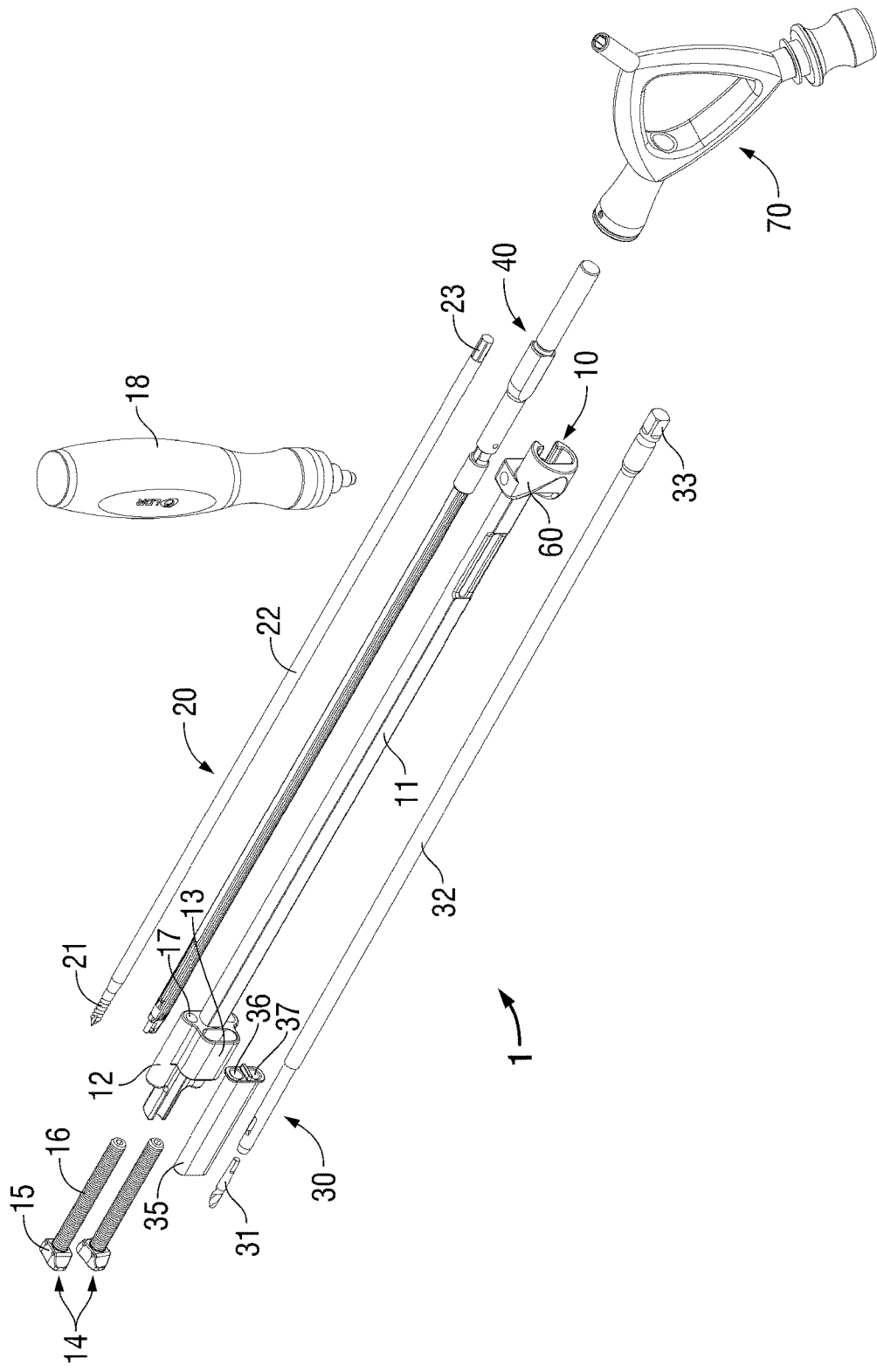
FIG. 1 depicts various components of an embodiment of an anchor removal instrument.
Figure 14:
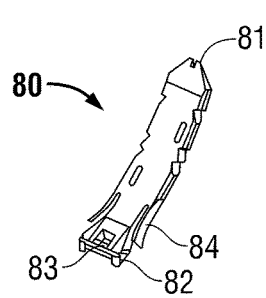
FIGS. 14 and 15 depict an embodiment of an anchor for an implant.
Figure 15:
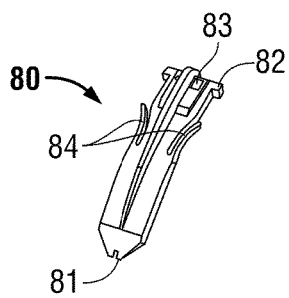

FIG. 1 depicts one of many possible embodiment of an instrument (1) for removing fixation devices of intervertebral implants. The example shown in FIG. 1 is implemented with features particularly useful for extracting a plate-like anchor, for example as depicted in FIGS. 14 and 15, but other instrument embodiments can be implemented with features useful for extracting other types of anchors or for fixation structures such as pins, nails, screws, staples, etc.

The embodiment of instrument (1) illustrated in FIG. 1 comprises a support (10), a support retainer or coupler (20), a drill assembly (30), a drill guide (35), an extractor (40), an extractor support (60), and an operation handle (70). In this embodiment, the support assembly (10) is configured with support and stabilization handle (18), and as depicted for example in FIG. 2, with support tube (11), support head (12), and extractor support (60). Support head (12) and/or extractor support (60) can be separate components, or made integral with support assembly (10). FIG. 3 depicts further detail of support head (12) of this embodiment, showing a drill guide support made integral with an extractor guide (in structure 13).

The embodiment of FIG. 3 is configured with a separate support head (12) attached to support tube (11), which can be accomplished with conventional structures such as threads, pins, screws, adhesives, solder, etc. Support head (12), however, could be integral with tube (11) in other embodiments. Support head (12) in this embodiment has drill guide support and extractor guide (13) configured as an oblong channel surrounded by a hood, but the drill guide support and extractor guide may also be deployed as separate elements at other locations of instrument (1), for example as various configurations of channels, eyes, loops, hooks, hoods, brackets, etc. The illustrated embodiment of support head (12) also provides for attachment of separate contact surfaces to maintain the support head (12) at a particular distance from the vertebrae or the implant, but similar contact surfaces in other embodiments may be made integral with head (12). In this example, contact surfaces are deployed with depth stops (14) that are devised as bumpers (15) with the contact faces, and bumpers (15) are supported on bumper supports (16) configured as threaded rods. Head (12) in this embodiment has contact surface supports 17 configured as threaded drillings in head (12). Threaded rods (16) engage the threaded drillings (17) in this embodiment, thus allowing for the distance between the contact surfaces of bumpers (15) and the support head (12) to be adjusted by screwing rods (16). In the illustrated embodiment of FIG. 1, the contact surfaces of depth stops (14) are configured to abut the respective adjacent vertebrae, but in other embodiments one or more contact surfaces may be deployed, and one or more (or all) of the contact surfaces may optionally be configured to abut the implant instead of a vertebra.

In various embodiments, a coupler or retainer may be configured to fix the support assembly (10) to the implant or otherwise retain the support assembly (10) fixed with respect to the implant. For the embodiments illustrated in FIGS. 1-3, support tube (11) is configured with a channel extending the length of tube (11), through which attachment screw (20) can pass. Attachment screw (20) in this example comprises screw tip (21), screw shaft (22), and screw drive adapter (23). In the embodiment illustrated in FIG. 1, screw tip (21) is deployed with self tapping threads. Rotation of this attachment screw (20) with tip (21) engaged in the implant, for example a hole deployed on an exposed surface of the implant, will cause the threads of tip (21) to engage the implant. In this way, a shoulder or similar blocking structure of shaft (22) can be drawn to abut a corresponding blocking structure in shaft (11) or head (12), causing support assembly (10) to be fixed to the implant or at least be held fixed with respect to the implant. Alternative to self-tapping threads on tip (21) include machine threads, interrupted threads, tapered threads, locking lugs, pins, and other structures that can mate with corresponding structures of the implant to hold the support assembly (10).

The illustrated embodiment uses a hex-headed screw drive adapter (23) connected to the tip (21) by shaft (22), but other configurations to actuate the coupling or retaining structures can be used. For example, the coupling or retaining structures could be actuated by a reciprocating rod that, in an activated position, causes lugs or other locking means to move into engagement with corresponding latching structures of the implant, and in an inactivated position, causes the lugs or other locking means to retract from the corresponding latching structures of the implant.

In some implant embodiments, access to the anchoring device may be obscured by part of the implant. For these types of implants, the anchor removal instrument may be deployed with means to expose a portion of the anchoring device so that the anchoring device can be grasped by an extractor. Such means may provide access to the anchoring device, for example, by opening, separating, moving, or removing portions of the implant. In the embodiment of an anchor removal instrument (1) depicted in FIG. 1, for example, a drill assembly (30) is provided to drill access holes in the implant through which the anchors can be grasped. This embodiment of drill assembly (30) comprises a drill bit (31), which may be deployed in any format appropriate for the implant material, including a spade, brad point, or twist bit, a hole saw, or an end mill. Drill bit (31) also may be deployed as a hollow shaft Forstner bit driven by a hollow drill shaft (32), which would allow the application of suction through the shafts to the drilling site to draw away chips and other debris from the drilling operation.

FIG. 3 also depicts an embodiment of a drill guide (35) used to support drill assembly (30) and direct drill bit (31) to an appropriate location on the implant when drilling the implant to gain access to the anchors. This embodiment of drill guide (35) may be implemented in various materials, such as steel, aluminum, titanium, plastic, etc. The illustrated embodiment is deployed as an elongated bar with rounded corners having a profile that complements the profile of a channel in the drill guide support and extractor guide (13). This embodiment also has upper guide (36) and lower guide (37), which are provided by borings along the length of the body of guide (35). Preferably, the illustrated embodiment is arranged so that when support assembly (10)

is fixed to the implant using attachment screw (20), upper guide (36) and lower guide (37) are located to directly guide drill bit (31) to the respective locations of the implant appropriate to gain access to the anchors and to hold drill bit (31) in that location during the drilling operation.

Drill guide (35) can be inserted in or removed from drill guide support (13) in the embodiment illustrated in FIGS. 1 and 3. When drill guide (35) is removed in this embodiment, structure (13) may also be used as an extractor guide, as discussed further below. Accordingly, this example of drill guide (35) also has extraction tab (38), which may be used to extract the drill guide (35) from the drill guide support (13), for example by grasping tab (38) with forceps.

Figure 2:
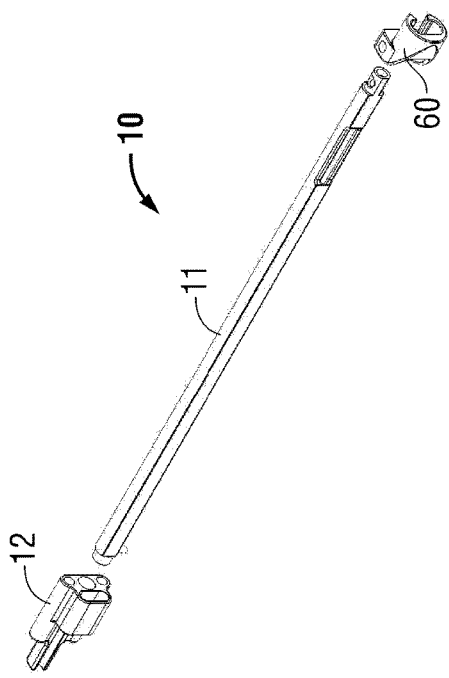
FIG. 2 depicts various components of an embodiment of a support assembly for the device of FIG. 1.
Figure 3:
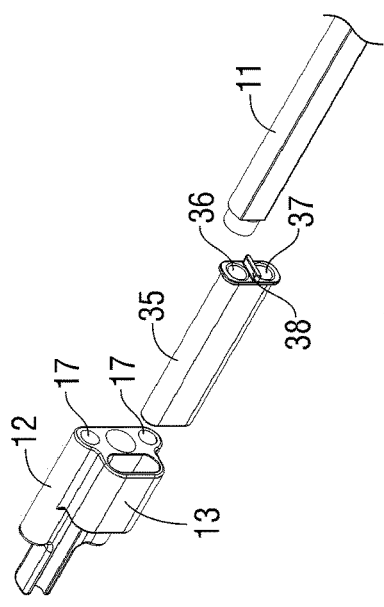
FIG. 3 depicts further details of the components depicted in FIG. 2.
Figure 5:
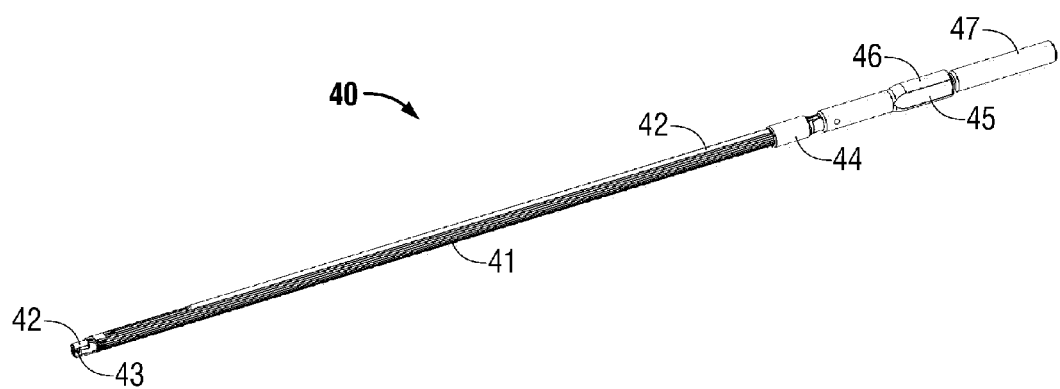
FIG. 5 depicts the extractor assembly of the instrument depicted in FIG. 1.

In the embodiments illustrated in FIGS. 1-3 are supported with respect to the implant by attachment screw (20) and ends the anchors fixing the implant to the vertebrae have been exposed using drill assembly (30) and drill guide (35), the equipment usually will be ready to extract the anchors. For many types of embodiments, an extra assembly similar to the embodiment shown in FIG. 5 will be appropriate for extracting the anchors. The extractor assembly (40) embodiment illustrated in FIG. 5 comprises extractor shaft (41), anchor attachment rod (42), attachment hook (43), and anchor attachment rod control (44).

Figure 6:
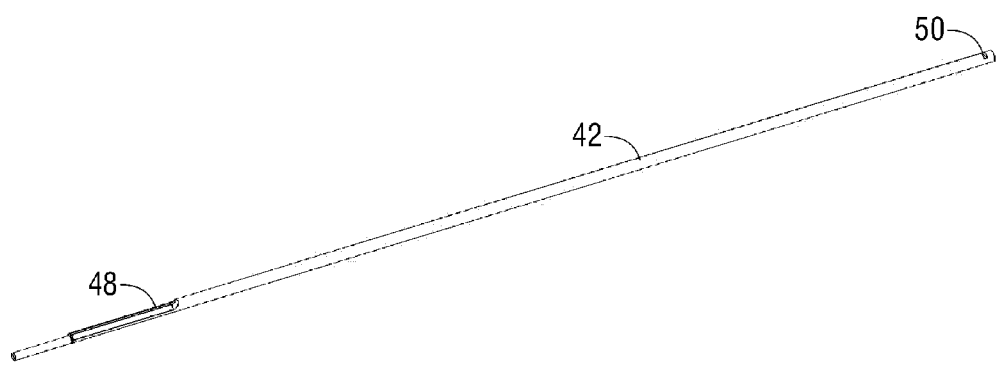
FIG. 6 depicts the anchor attachment rod of the extractor assembly depicted in FIG. 5.
Figure 7:
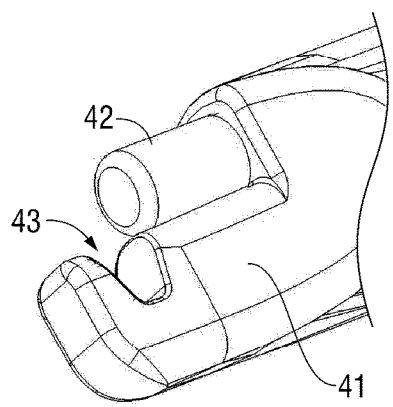
FIGS. 7 and 8 depict various components of the extractor assembly depicted in FIG. 5, with the anchor attachment rod in an open position in FIG. 7 and a closed position in FIG. 8.
Figure 8:
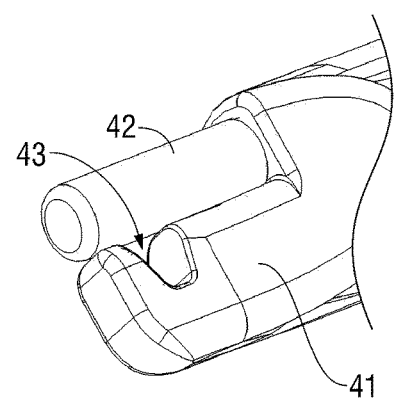
Figure 9:
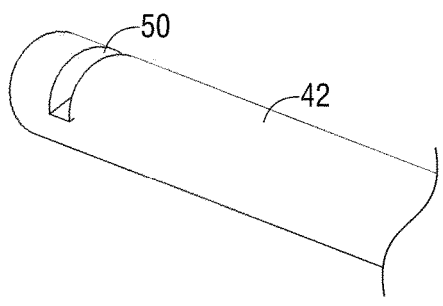
FIG. 9 depicts the structure of an end of the anchor attachment rod depicted in FIG. 6.
Figure 10:
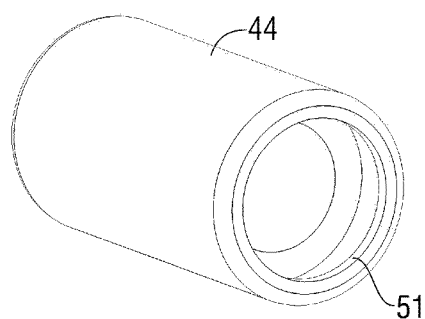
FIG. 10 depicts the anchor attachment rod control of the extractor assembly depicted in FIG. 5.
Figure 11:
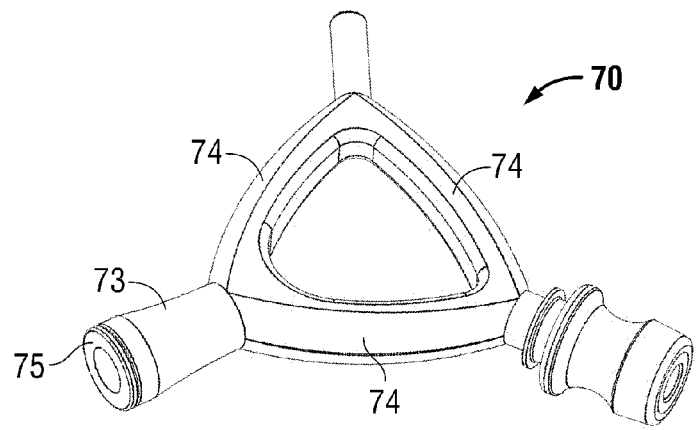
FIGS. 11-13 depict an operating handle for the extractor assembly depicted in FIG. 5.
Figure 12:
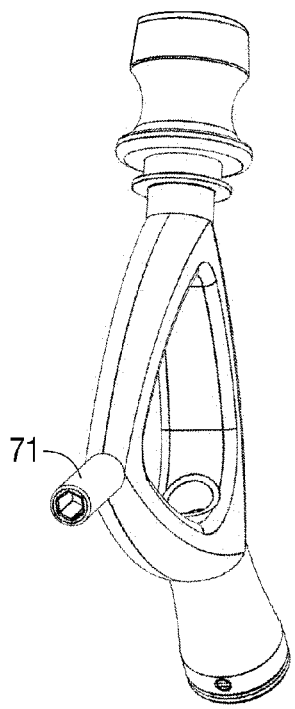
Figure 13:
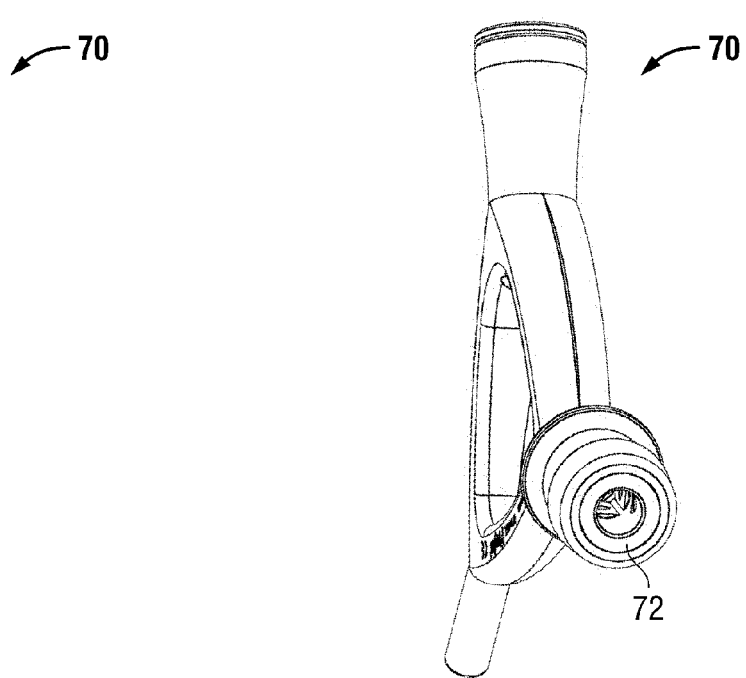

For the embodiment shown in FIGS. 5-10, anchor attachment rod (42) reciprocates in a channel disposed along a longitudinal edge of extractor shaft (41). The channel in this embodiment terminates near the hook end of shaft (41) in a bore disposed through the body of shaft (41). The end of rod (42) in this embodiment passes through the bore and may reciprocate in the bore, and the shaft material surrounding the bore retains the rod (42) against the shaft (41). For this embodiment, the hook end of rod (42) is cylindrically shaped and sized to pass smoothly through the bore near the end of shaft (41), and the exterior facing surface of rod (42) near this end is recessed (48) to reduce the profile of extractor assembly (40) to provide extra clearance in the surgical opening. Near the other end of rod (42) in this embodiment, a notch (50) is disposed as shown in FIGS. 6 and 9. This notch receives rim (50) disposed circumferentially around the interior bore of a cylindrically shaped anchor attachment rod control (44). In this embodiment, control (44) is deployed with interior threads that engage exterior threads along shaft (41), with rotation of control (44) causing it to move along the longitudinal axis of shaft (41). This longitudinal movement of control (44) causes rod (42) to move linearly along the longitudinal axis of shaft (41), due to the engagement of rim (51) in notch (50).

The linear movement of rod (42) along the side of shaft (41) in the illustrated embodiments opens and closes attachment hook (43) disposed at an end of shaft (41), for example as depicted in FIGS. 7 and 8, to function as an anchor attachment or retainer. When the hook (43) is open as shown in FIG. 7, a grasping structure on an anchor can be placed in the open area of the hook. When the hook (43) is closed as shown in FIG. 8, the anchor is locked to shaft (41) by rod (42) as shown, for example, in FIGS. 41 and 44-48.

Figure 4:
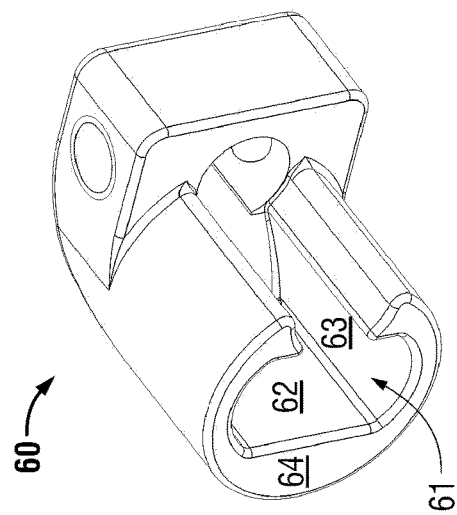
FIG. 4 depicts the extractor support/guide of the instrument depicted in FIGS. 1 and 2.

In the illustrated embodiments, the extractor assembly (40) may be supported at the end opposite hook (43) by an extractor support (60). Extractor support (60) is a removable structure in these embodiments, but other embodiments may have support (60) integrally formed with support assembly (10) or permanently or semi-permanently attached to support assembly (10). For the embodiment depicted in FIG. 4, extractor support (60) comprises an extractor guide channel (61), a flat channel surface (62), a pair of curved channel surfaces (63), and a bearing surface (64). In these embodiments, to put the extractor assembly (40) in place to extract an anchor, the hook end of extractor assembly (40) first is inserted through channel 61 and then through extractor guide (13). Then, this extractor assembly (40) is further pushed toward the implant until the flat channel engagement surface (45) of shaft (41) is adjacent to flat channel surface (62) of channel (61), and the curved channel engagement surfaces (46) of shaft (41) are respectively adjacent to curved channel surfaces (63) of channel (61). In this way, extractor assembly (40) has an appropriately limited range of linear movement in which the cooperation of the curved and flat surfaces of the respective components of shaft (41) and support (60) inhibit rotation of shaft (41); thus, support (60) serves also as an extractor guide. In this limited range, a withdrawing force can be transmitted to the anchor far enough to extract it from the implant without shaft (41) rotating. In these embodiments, this configuration allows the anchor withdrawing force to originate by rotating a threaded handle, such as the examples illustrated in FIGS. 11-13 and 42-43, on mating threads of attachment adapter (47). This rotation of handle (70) causes shaft (41) to move linearly away from the implant, causing the anchor attachment/retainer (e.g., hook 43 and tip of rod 42) to exert the withdrawing force on the anchor. For withdrawal of curved anchors, for example as illustrated in FIGS. 41 and 44-46, the oblong shape of the channel in extractor guide (13) allows the hook end of shaft (41) to rise and fall in the channel, thus accommodating the curved path the anchor follows in its extraction from the implant.

An extraction actuator may take forms other than the illustrated handles (70). For example, linear or rotational ratchet assemblies may be useful in some situations, and in some situations with particularly firmly seated anchors, a slide hammer configuration may be indicated. In many routine situations, though, an actuator such as the illustrated handles (70) will be preferred. The handle (70) embodiment illustrated in FIGS. 11-14 has an extraction adapter (73) configured to engage attachment adapter (47) of extractor shaft (41) for extraction of an anchor. For example, threads in adapter (73) may engage corresponding threads on adapter (47). In this example, shaft (41) is inserted in support/guide (60) as far as needed to attach to the anchor and retain the anchor to the shaft (41). Then, handle (70) is rotated to thread it onto adapter (47) using adapter (73), until bearing surface (75) of adapter (73) abuts bearing surface (64) of extractor support/guide (60). At this point, further rotation of handle (70) causes shaft (41) to move linearly away from the implant, thus extracting the anchor from the implant.

The actuation handle (70) embodiment illustrated in FIGS. 1 and 11-13 provides other features, too. For example, hex drive adapter (71) is configured to mate with screw drive adapter (23), allowing handle (70) to be used to drive screw shaft (22). This embodiment also provides square drive adapter (72) configured to mate with drill drive adapter (33) allowing the handle to rotate shaft (32). Such hand powered drilling may be sufficient in many situations, but some embodiments may instead use a power drive for drill assembly (30). Any of these types of adapters may be deployed with locking mechanisms for mating adapters, and may have quick-release configurations for such mechanisms. For example, when a collar is in a first "hold" position, a ball detent in adapter (72) could firmly hold drive adapter (33) in adapter (72), and when the collar is in a second "released" position, pressure on the ball detent would be removed and drive adapter (33) released.

The embodiment shown in FIG. 1 is particularly adapted for use with curved-plate type anchors, such as those described in International Application No. PCT/IB2009/008048. Other embodiments, however, may be adapted for other types of anchors (straight and curved) and retaining structures, e.g., pins, staples, screws, nails, etc. FIGS. 14-20 depict examples of anchors for which the embodiment shown in FIG. 1 is particularly useful. The anchor (80) embodiment illustrated in FIGS. 14-19 has is generally curved along its length, with an insertion tip (81) configured for insertion in a vertebral structure at one end and a retainer (82) at the other end, which prevents over-insertion of the anchor in the implant (90). These embodiments also have latches (84), which hold the anchor (80) in the implant (90) after full insertion of the anchor, and a withdrawal opening (83). This withdrawal opening (83) comprises an open area through the anchor (80), allowing grasping of the anchor.

Figure 16:
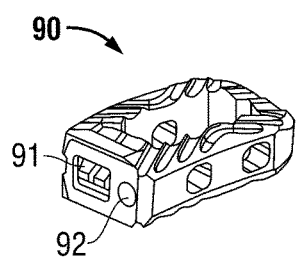
FIG. 16 depicts an implant configured for use of the anchor depicted in FIGS. 14 and 15.
Figure 17:
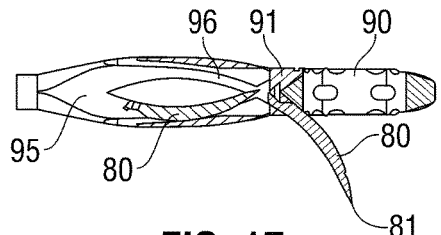
FIGS. 17-18 and depict an insertion instrument used to place an implant and deliver anchors through the implant into adjacent vertebrae.
Figure 18:
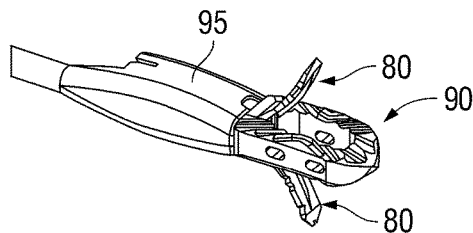
Figure 19:
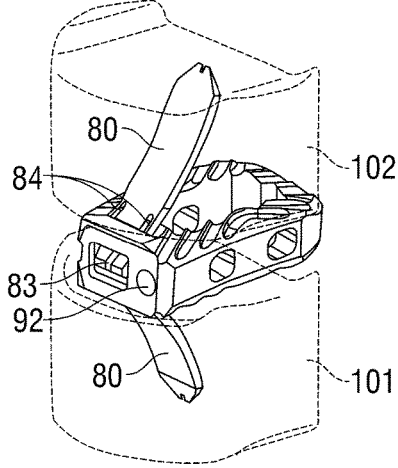
FIG. 19 depicts the anchor of FIGS. 14-15 and the implant of FIG. 16 implanted between two vertebrae.
Figure 20:
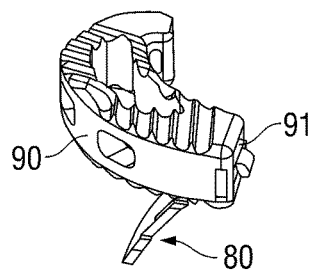
FIG. 20 depicts an embodiment of an implant and anchor combination suitable for transforaminal lumbar interbody fusion.

FIGS. 16-19 depict an embodiment of an implant (90) useful with the anchor (80) embodiment illustrated in FIGS. 14 and 15, and with other types of anchors as well. This embodiment has an attachment hole (92), which is useful both during implantation of the implant and for retaining the anchor removal instrument (1) during any extraction of an anchor. For example, using the attachment screw (20) embodiment of FIG. 1, screw tip (21) can be turned into attachment hole (92) causing support assembly (10) to be fixed to the implant or at least be held fixed with respect to the implant. The embodiment depicted in FIGS. 16-19 also comprise anchor guide slots (91), which allow anchor (80) to be inserted into implant (90) and driven into an adjacent vertebra through a surgical approach in surrounding tissue that need only be large enough to pass the implant (80). An embodiment of an insertion head (95) that facilitates this minimally invasive approach is depicted in FIGS. 17 and 18, showing anchor insertion channels (96) that are used to guide the anchor (80) along its arc-shaped route into the implant (80) and then an adjacent vertebra. FIG. 19 shows the use of these embodiments in an implantation of implant (90) between two vertebrae, illustrating the insertion of anchors (80) into those vertebrae. FIG. 20 shows an implant (90) embodiment useful for transforaminal lumbar interbody fusion, using a single anchor (80), but the general structures and steps applicable to the embodiments of FIGS. 14-19 are also applicable to this arrangement. FIGS. 16 and 20 show examples of implants for which an anchor removal instrument may be useful, but appropriately configured anchor removal instruments may be useful for other implants (including intervertebral prostheses and intersomatic cages) that use one or more anchors or other retaining structures.

FIGS. 21-49 depict an example of anchor withdrawal using embodiments of anchor removal instrument (1) previously described. The following discussions are directed to those particular embodiments, but are not restrictive as to other embodiments of structures or methods.

Figure 23:
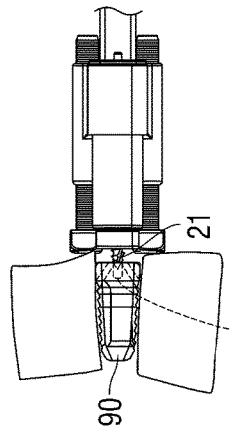
FIGS. 21-49 depict a method of using the embodiments depicted in FIGS. 1-13.
Figure 24:
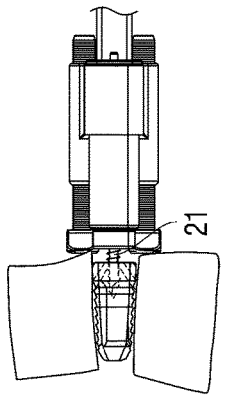
Figure 25:
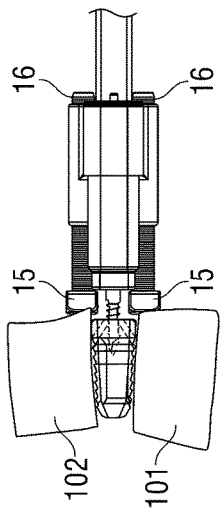
Figure 21:
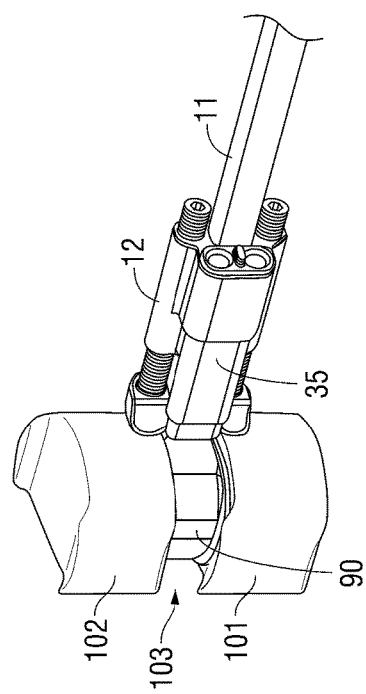
Figure 22:
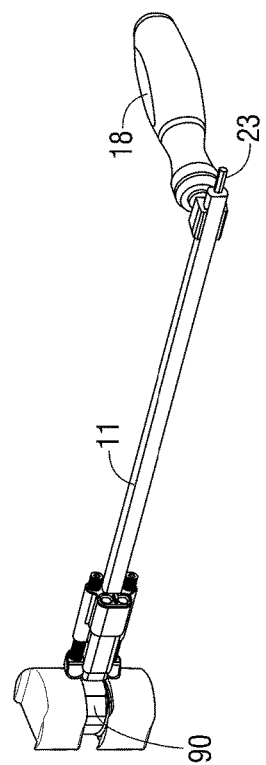

FIG. 21 depicts initial placement of an anchor removal instrument (1) near an implanted implant (90) after the surgical approach to the intervertebral space is obtained. It is convenient to make initial placement of support head (12) with drill guide (35) in place in the drill guide support (13). Attachment screw (20) may already be inserted partially in the channel of support tube (11), or may be inserted following initial placement of the head (12). With the attachment screw (20) in place as shown in FIG. 22, it is screwed in the implant (90), preferably into an attachment hole (92) in the implant, as shown in FIGS. 23-24. Drilling force is applied at screw drive adapter (23), either with a hand drive (for example, with handle (70) shown in FIGS. 11-13) or a power drive. The operative distance of head (12) from the vertebrae (101, 102) is set by adjusting bumper supports (16) in depth stop attachment holes (17) in support head (12), causing bumpers (15) to abut the respective vertebrae (101, 102) as shown in FIG. 25. Alternatively, if the circumstance allow (e.g., by providing sufficient working space), one or more bumpers (15) may be adjusted to abut the implant (90) instead of the vertebrae, or head (12) may itself directly abut the implant or one or more vertebrae. Regardless of the abutment configuration, a countervailing force preferably acts directly on the implant or a vertebra to counteract the extraction force exerted on the anchor during its extraction.

Figure 26:
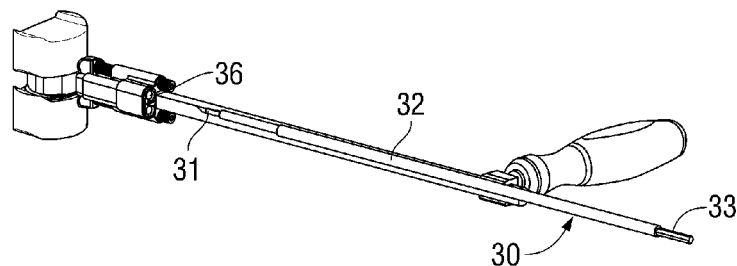
Figure 27:
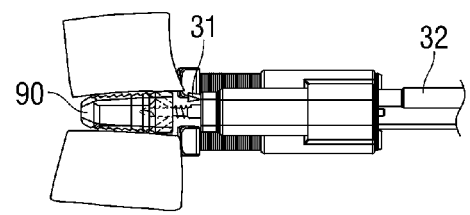
Figure 28:
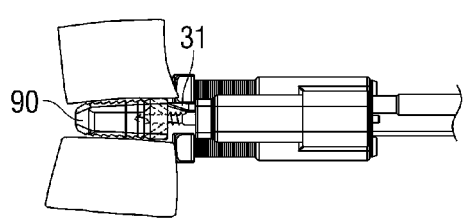
Figure 29:
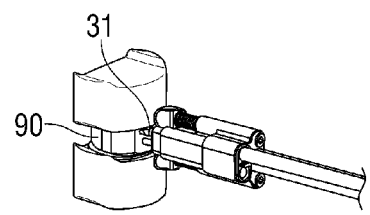
Figure 30:
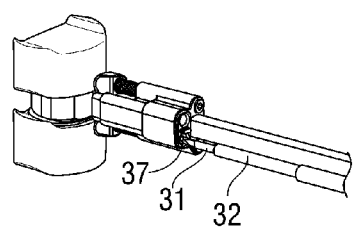
Figure 31:
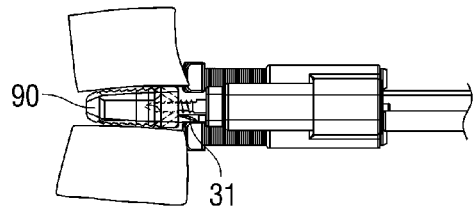

FIGS. 26-29 depict an example of steps that can be used to gain access to an anchor for grasping it. For example, drill assembly (30) is put in place to drill a hole in implant (90) to expose withdrawal opening (83) of a first anchor (80). FIG. 26 shows bit (31) approaching the outer opening of upper guide (36). FIG. 27 shows bit (31) emerging from the inner opening of upper guide (36). FIGS. 28 and 29 show bit (31) engaging implant (90) in the drilling operation. Following this drilling operation, withdrawal opening (83) of the first anchor (80) is exposed and can be grasped with hook (43) of extractor assembly (40). FIGS. 30 and 31 depict the use of lower guide (37) to direct and stabilize drill assembly (30) while drill bit (31) creates another opening in implant 90 to expose withdrawal opening (83) of a second anchor (80). Preferably, support assembly (10) is configured so that engagement of screw tip (21) into attachment hole (92) of the implant automatically aligns upper guide (36) and lower guide (37) in proper position for drilling optimally located holes in implant (90) to gain optimal access to the withdrawal openings (83) of the anchors (80).

Figure 32:
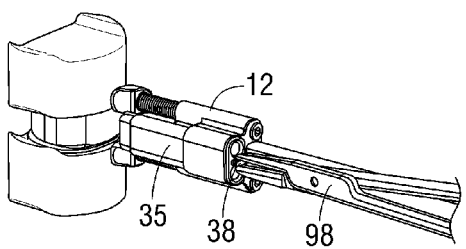
Figure 33:
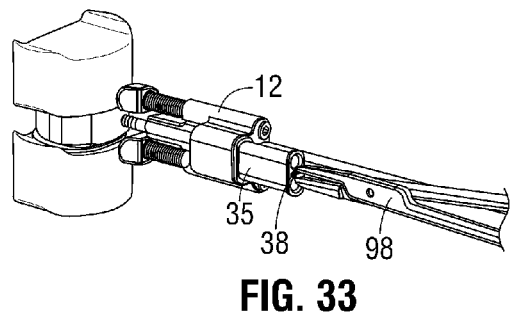

Once the access to withdrawal openings (83) of the anchors (80) is obtained, drill guide (35) can be removed from drill guide support (13). FIGS. 32 and 33 show forceps (98) being used to grasp extraction tab (38) on drill guide (35) and pull the tab (38) to withdraw the guide (35) from the support (13).

Figure 34:
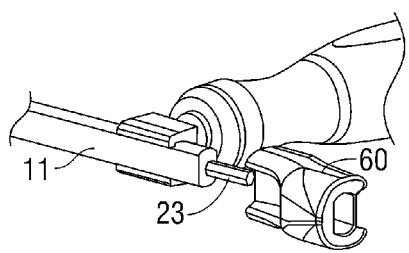
Figure 35:
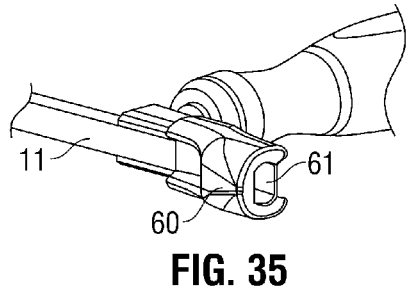

FIGS. 34 and 35 depict extractor support/guide (60) being placed on support tube (11). Other embodiments that use an extractor support/guide, however, may have the support/guide (60) permanently attached or made integral with tube (11) or another structure of instrument (1).

Figure 36:
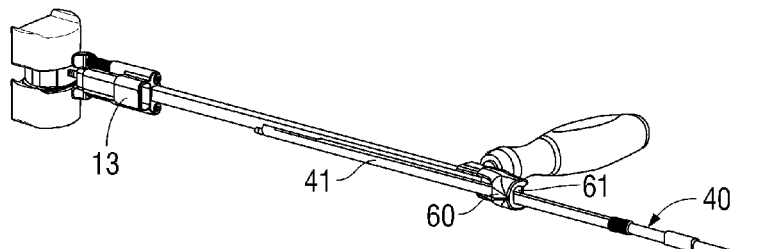
Figure 37:
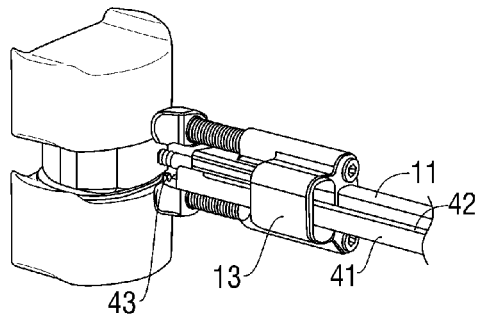
Figure 38:
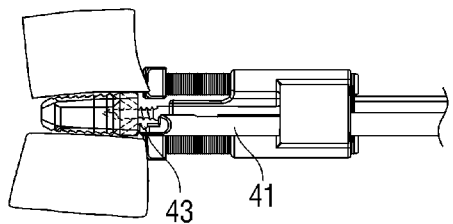
Figure 39:
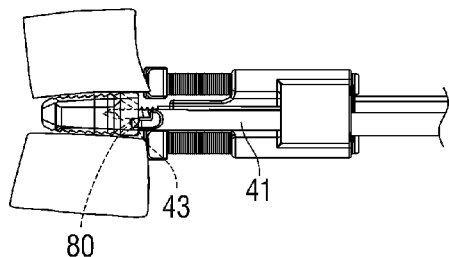
Figure 40:
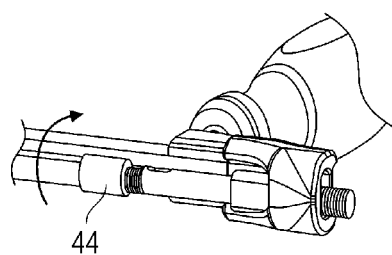
Figure 41:
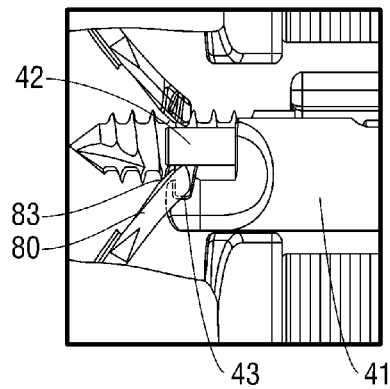

FIGS. 36 and 37 depict the placement of extractor assembly (40). In this example, attachment hook (43) is inserted through extractor guide channel (61) of extractor support/guide (60) and through the oblong channel of extractor guide (13). As shown in FIGS. 37-39, anchor attachment rod (42) is retracted to leave attachment hook (43) open to grasp the end of anchor (80) using withdrawal opening (83) of the anchor. With the rear of anchor (80) in place in the notch of attachment hook (43), anchor attachment rod control (44) is rotated to urge anchor attachment rod (42) forward to close attachment hook (43), as shown for example in FIGS. 40 and 41. Anchor (80) is now securely attached to and retained by extractor assembly (40).

Figure 42:
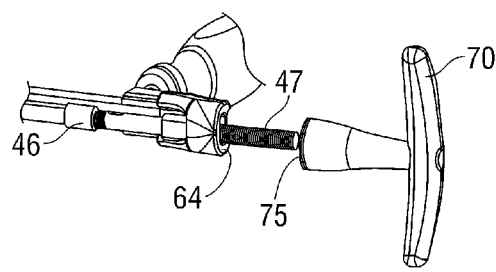
Figure 43:
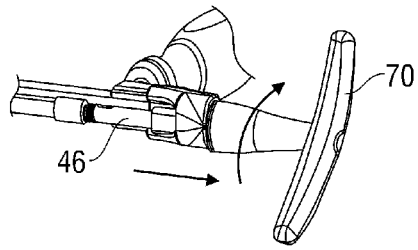
Figure 44:
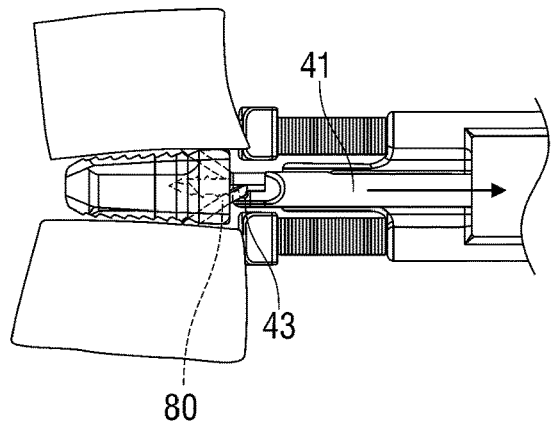
Figure 45:
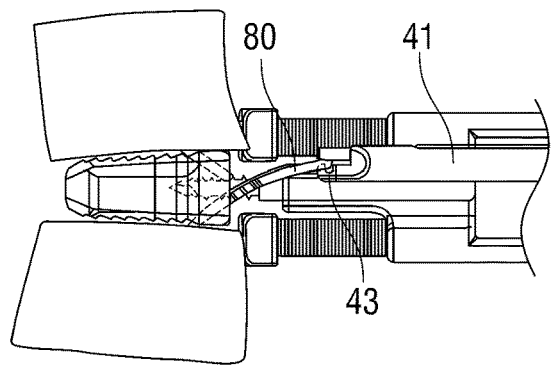
Figure 46:
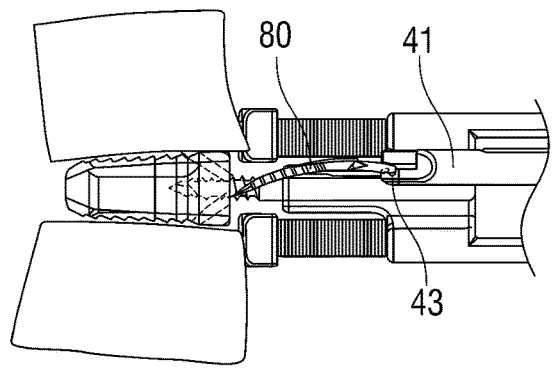

In the illustrated embodiments, handle (70) is screwed onto threads disposed along attachment adapter (47) until bearing surface (64) of extractor support (60) contacts bearing surface (75) of handle (70), for example as shown in FIGS. 42 and 43. Further rotation of handle (70) causes extractor shaft (41) to move linearly away from the implant (90), as depicted in FIG. 43. This linear movement of extractor shaft (41) causes hook to pull anchor (80) out of the vertebra and the implant, for example as shown in FIGS. 44-46. If necessary, sufficient force is applied to anchor (80) to overcome any latches (84) or other retention means holding the anchor in the implant. FIGS. 44-46 illustrate that the oblong channel in guide (13) permits hook (43) to rise and fall as necessary to accommodate the extraction path of anchor (80).

Figure 47:
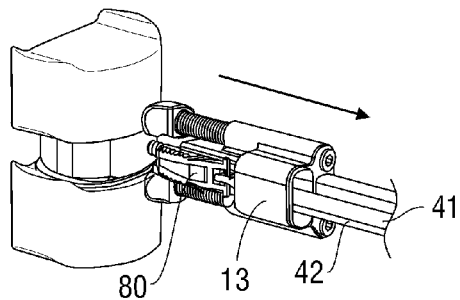
Figure 48:
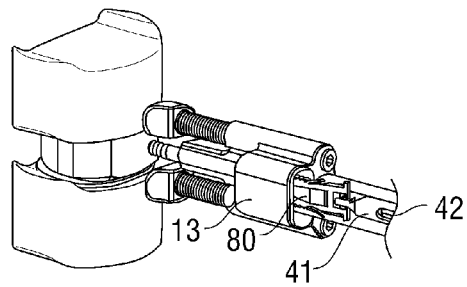
Figure 49:
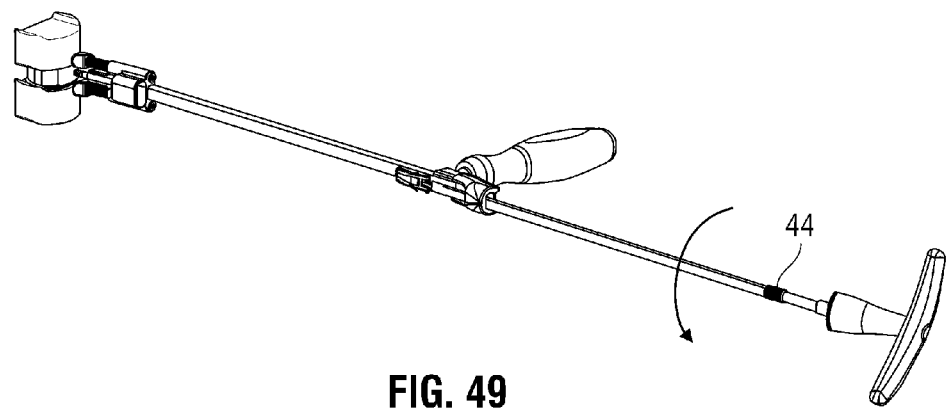

Anchor (80) can now be withdrawn through the channel in extractor guide (13). If necessary due to the relative widths of anchor (80) and the channel in guide (13), anchor (80) may be rotated by rotating shaft (41) and then withdrawn through the channel, for example as shown in FIGS. 47-48. When the anchor (80) is away from the surgical approach area, it can be removed from hook (43) by reversing the rotation of anchor attachment rod control (44), thus withdrawing anchor attachment rod (42) and opening attachment hook (43) to release anchor (80), for example as shown in FIG. 49. The foregoing method may be repeated for any additional anchors that need to be withdrawn.

The foregoing example of anchor extraction using embodiments of anchor removal instrument (1) previously described is merely representative. Various steps may or may not be required, or additional or modified steps may be required, depending on the particular embodiments of implants, anchors, and extraction tools used, and various embodiments of extraction tools may be used depending on the steps performed and the implants and anchors involved. It also should be noted that in multi-anchor implants, it may not be necessary to remove all anchors prior to removal of the implant. For example, an implant and associated anchors could be configured so that the implant could be removed after extraction of one anchor (80) by pulling on the implant and causing the implant itself to extract the remaining anchor during withdrawal of the implant.

After appreciating this disclosure, those of skill in the art will recognize that the steps of the various methods, processes, and other techniques disclosed herein need not be performed in any particular order, unless otherwise expressly stated or logically necessary to satisfy expressly stated conditions. In addition, after appreciating this disclosure those skilled in the art will recognize that the invention may be embodied in a variety of different forms and that various changes, substitutions, and alterations can be made without departing from the spirit and scope of the invention. References herein to surfaces or other structures as "upper," "top," "lower," "bottom," "inner," "outer," or having a "height," "width," or "length," and directional references such as "horizontal" and "vertical," are generally arbitrary and for convenience only, and those of skill in the art will recognize after appreciating this disclosure that such designations appropriately may be reoriented in particular embodiments. The described embodiments are illustrative only and are not restrictive, and the scope of the invention is defined solely by the following claims.

The invention claimed is:

1. A tool for removing an anchor from an intervertebral implant comprising:
   an elongated support comprising a vertebral body bumper at a first end of the support and a stabilization handle disposed perpendicular to the elongated support proximal to a second end of the elongated support;
   a coupler configured to fix the support to the implant;
   an elongated extractor comprising an anchor attachment at one end of the extractor and an extraction actuator, the anchor attachment adapted to couple to an anchor disposed within a channel of the intervertebral implant;
   an extractor guide disposed along the support proximal to the first end of the support; and
   an extractor support disposed along the support proximal to the second end of the support, wherein the elongated extractor is supported by the extractor support and guided, by the extractor guide, into engagement with the anchor to facilitate coupling the anchor attachment with the anchor for removal of the anchor from the channel of the intervertebral implant.

2. The tool of claim 1 in which the coupler comprises a rod with screw threads on one end and a drive adapter on another end.

3. The tool of claim 2 in which the elongated support further comprises a tube extending between the first end of the support and the second end of the support, the tube configured to hold the coupler.

4. The tool of claim 1 further comprising a drill.

5. The tool of claim 4 in which the elongated support further comprises a head and a removable drilling guide receivable in the head.

6. The tool of claim 1 in which the anchor attachment comprises a hook and a closure configured to grasp an anchor.

7. An instrument for removing an anchor from an intervertebral implant comprising:
   a support comprising a vertebral body bumper and a stabilization handle;
   a coupler configured to fix the support to the implant;
   an extractor comprising an anchor attachment and an extraction actuator, wherein the anchor attachment comprises a hook and a sliding rod closure mechanism; and
   an extractor guide disposed along the support.

8. The instrument of claim 7 in which the coupler comprises a screw.

9. The instrument of claim 7 in which extraction actuator comprises a handle.

10. The instrument of claim 7 in which the extractor further comprises a rod extending between the anchor attachment and the extraction actuator.

11. An intervertebral implant anchor extractor tool comprising:
    a support comprising a stabilization handle;
    a support retainer configured to hold the support fixed with respect to an implant;
    an extractor having an anchor retainer, the anchor retainer including a clamp comprising a hook and a tip of a slidable rod; and
    an extractor guide.

12. The anchor extractor tool of claim 11 in which the extractor comprises guide surfaces configured to mate with complementary surfaces of the extractor guide.

13. The anchor extractor tool of claim 12 in which the guide surfaces comprise a planar surface configured to mate with a complementary planar surface of the extractor guide.

14. The anchor extractor tool of claim 11 in which sliding of the slidable rod is controlled by a rotating knob encircling the slidable rod.

15. A vertebral implant system comprising the anchor extractor tool of claim 11, an implant anchor, an implant having a pathway configured to receive the anchor from a side of the implant and guide the anchor into a vertebral endplate, and a tool configured for insertion of the anchor to the implant and a vertebral endplate.

16. The vertebral implant system of claim 15 in which the anchor comprises a body having at least one curved plate elongated along a longitudinal axis extending between a penetration end of the anchor and a driving end of the anchor, and a longitudinal rib extending along at least part of a face of the plate.

* * * * *